US006939982B2

(12) United States Patent
Hoveyda et al.

(10) Patent No.: US 6,939,982 B2
(45) Date of Patent: Sep. 6, 2005

(54) RECYCLABLE CHIRAL METATHESIS CATALYSTS

(75) Inventors: Amir H. Hoveyda, Belmont, MA (US); Joshua Van Veldhuizen, Watertown, MA (US); Steven B. Garber, Brighton, MA (US); Jason S. Kingsbury, Brookline, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 10 days.

(21) Appl. No.: 10/435,777

(22) Filed: May 12, 2003

(65) Prior Publication Data

US 2004/0019212 A1 Jan. 29, 2004

Related U.S. Application Data

(60) Provisional application No. 60/380,640, filed on May 15, 2002.

(51) Int. Cl.[7] ........................ C07F 15/00; C07C 255/00
(52) U.S. Cl. ........................ 556/21; 556/136; 558/357; 558/462; 548/103
(58) Field of Search ........................... 548/103; 556/21, 556/136; 558/357, 462

(56) References Cited

U.S. PATENT DOCUMENTS 6,590,048 B1     7/2003    Fürstner et al. ............. 526/171

OTHER PUBLICATIONS

Copy of International Search Report, dated Oct. 20, 2003.
Garber, et al., Efficient and Recyclable Monomeric and Dendritic Ru–Based Metathesis Catalysts, *Journal of the American Chemical Society*, vol. 122, No. 34: 8168–8179 (2000).

Kingsbury, et al., A Recyclable Ru–Based Metathesis Catalyst, *Journal of the American Chemical Society*, vol. 121, No. 4: 791–799 (1998).

Gessler, et al., Synthesis and Metathesis Reactions of a Phosphine–free Dihydroimidazole Carbene Ruthenium Complex, *Tetrahedron Letters*, No. 51: 9973–9976 (2000).

Harrity, et al., Chromenes through Metal–Catalyzed Reactions of Styrenyl Ethers, Mechanism and Utility in Synthesis, *Journal of the American Chemical Society*, vol. 120, No. 10: 2343–2351 (1997).

Randl, et al., Highly Selective Cross Metathesis with Acrylonitrile Using a Phosphine Free Ru–Complex, *Synlett*, No. 3: 430–432 (2000).

Harrity, et al., Ru–Catalyzed Rearrangement of Styrenyl Ethers. Enantioselective Synthesis of Chromenes through Zr– and Ru–Catalyzed Processes, *Journal of the American Chemical Society*, vol. 119; 1488–1489 (1996).

*Primary Examiner*—Porfirio Nazario-Gonzalez
(74) *Attorney, Agent, or Firm*—Palmer & Dodge, LLP; Paula Campbell Evans; David J. Dykeman

(57) ABSTRACT

The present invention relates to chiral metal catalysts for stereoselective olefin metathesis reactions, which are recyclable and reusable in such metathesis reactions. The chiral metal-based metathesis catalysts of the invention comprise multidentate optically active or racemic chiral ligands that enable their use in asymmetric synthetic processes, such as for example, in ring-opening and ring-closing metathesis reactions (ROM and RCM, respectively) of alkenes. The catalysts of the invention are organometallic complexes of multivalent metals comprising one or more chiral bidentate ligands that exhibit superior reactivity and stereoselectivity properties. The present invention also provides methods of making such catalysts and methods for utilizing them in catalyzing stereoselective olefin metathesis reactions to provide asymmetric products in relatively high enantiomeric or stereoisomeric excess.

48 Claims, 1 Drawing Sheet

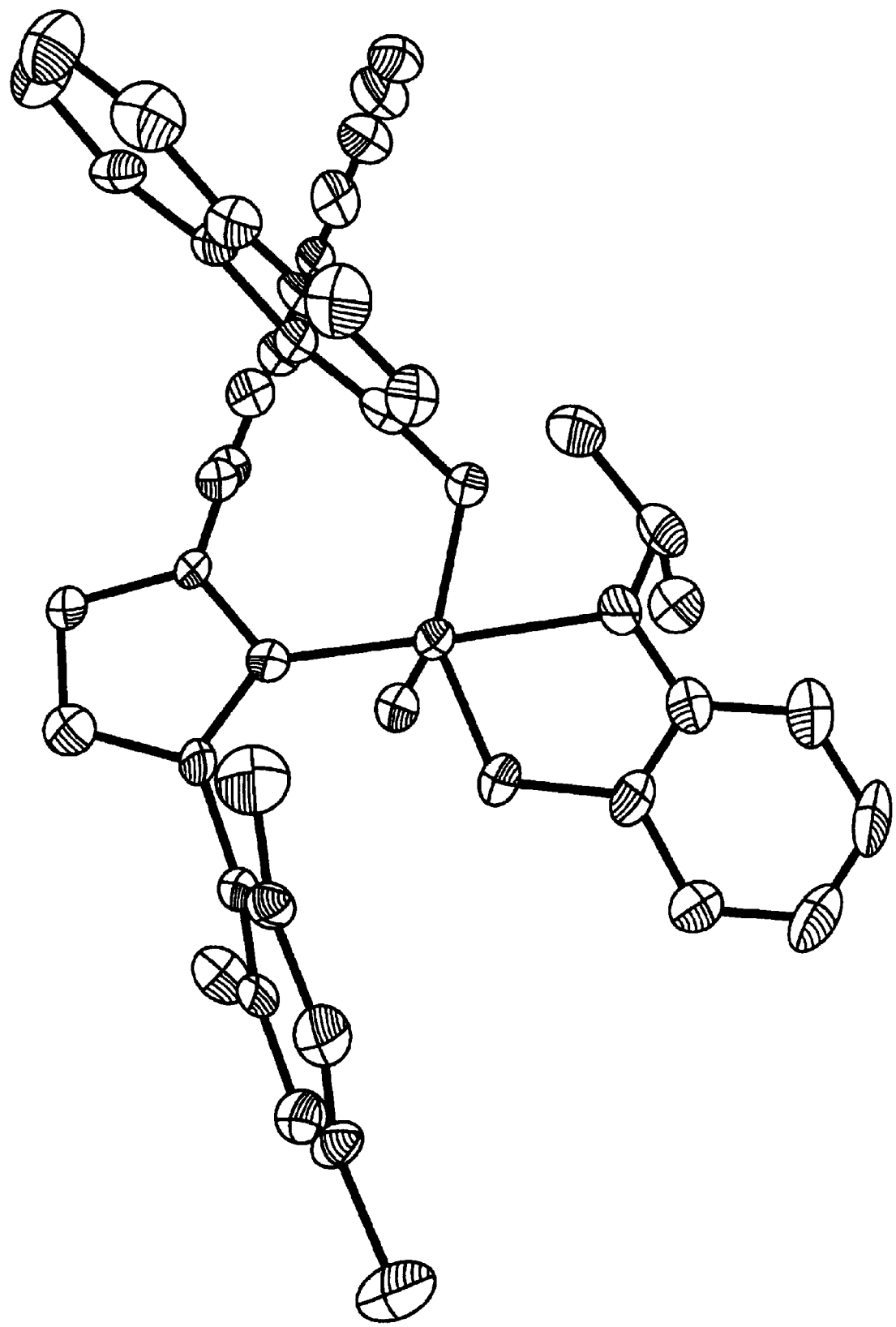

RECYCLABLE CHIRAL METATHESIS CATALYSTS

RELATED APPLICATION

This application claims the benefit of U.S. Provisional Application No.: 60/380,640, filed May 15, 2002. The entire teachings of the above application is incorporated herein by reference.

GOVERNMENT SUPPORT

The invention was supported, in whole or in part, by a grant No. CHE-9905806 from National Science Foundation. The Government has certain rights in the invention.

BACKGROUND OF THE INVENTION

Metal-catalyzed olefin metathesis reactions serve as a springboard for the development of a range of regioselective and stereoselective processes. These processes are important steps in the chemical synthesis of complex organic compounds and polymers. In particular, these reactions often are crucial steps in medicinal chemistry for small molecule synthesis. Organometallic catalysts, particularly transition metal complexes based on osmium, ruthenium or tungsten, are used in many such organic transformation reactions. The catalytic activity of a molybdenum-based chiral catalyst for asymmetric synthesis involving ring-closing metathesis (RCM) of terminal alkenes has been reported, for example, by La et al. *J. Am. Chem. Soc.*, (1998) 120, 9720. These catalysts however, are extremely air and moisture sensitive, thus limiting their applicability to a range of substrates containing terminal alkenes. Furthermore, due to their instability during product purification by chromatographic methods, the isolation of prior-art chiral metathesis catalysts from reaction products is often problematic.

SUMMARY OF THE INVENTION

The present invention relates to olefin metathesis catalysts for stereoselective synthesis capable of catalyzing substrates containing terminal and/or internal alkenes. The catalysts of the invention are both stable and recyclable. More particularly, the present invention relates to chiral transition metal catalysts for stereoselective olefin metathesis reactions. The present invention also relates to chiral transition metal catalysts that are recyclable and reusable in such metathesis reactions. The chiral transition metal-based metathesis catalysts of the invention comprise multidentate optically active or racemic chiral ligands (hereinafter referred to as "chiral ligands") that enable their use in asymmetric synthetic processes, such as for example, in ring-opening and ring-closing metathesis reactions (ROM and RCM, respectively) of alkenes. The catalysts of the invention are organometallic complexes of transition metals comprising one or more chiral bidentate ligands that exhibit superior reactivity and stereoselectivity properties. The catalysts of the invention can be in monomeric, polymeric or dendritic forms and are capable of promoting various forms of olefin metathesis reactions in a stereoselective manner. The present catalysts are efficiently recoverable from the reaction mixtures and reusable; they are therefore, recyclable. The present invention also provides methods of making such catalysts and methods for using them in catalyzing stereoselective olefin metathesis reactions.

In addition to their ability to form terminal alkenes, the catalysts of the present invention effect the efficient formation of polysubstituted olefins through catalytic metathesis processes in an enantioselective manner to provide asymmetric products in relatively high enantiomeric or stereomeric excess (ee and de respectively). Polysubstituted olefins can be di-substituted, tri-substituted, and tetra-substituted olefins. The polymeric and dendritic forms of the chiral catalysts of the invention offer the added advantage of being more readily isolable. Because they are active toward non-terminal alkene substrates, they can be used to synthesize tri- and tetra-substituted olefins. The chiral catalysts of the invention can be recovered (e.g., by standard filtration or chromatographic methods) leaving little or no trace of toxic metal contamination within the products, and can be reused in subsequent reactions.

In one aspect, the invention comprises a composition comprising a metal catalyst having the following Formula (1):

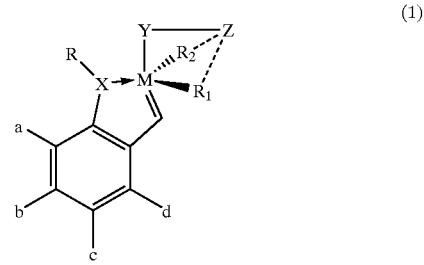

(1)

wherein:

M is a polyvalent metal. In a preferred embodiment, M is a transition metal comprising, for example, ruthenium (Ru), rubidium (Rb), rhodium (Rh), molybdenum (Mo) or tungsten (W).

X comprises oxygen (O) or sulfur (S);

R comprises an alkyl, alkenyl, alkynyl, aryl, aralkyl, alkoxy, alkenyloxy, alkynyloxy, aryloxy, alkoxy carbonyl, alkylamino, alkylthio, alkylsulfonyl, alkylsulfinyl; each optionally substituted with an alkyl, halogen, alkoxy, aryl or heteroaryl group;

$R_1$ and $R_2$ independently comprise electron-withdrawing ligands;

a, b, c, and d each comprise hydrogen (H), a halogen atom or an alkyl, alkenyl, alkynyl, aryl, aralkyl, alkoxy, alkenyloxy, alkynyloxy, aryloxy, alkoxycarbonyl, alkylamino, alkylthio, alkylsulfunyl; alkylsulfinyl; each optionally substituted with an alkyl, halogen, aryl or heteroaryl group; and Y comprises an electron-donating ligand. In one embodiment, Y comprises a heterocyclic group or a carbene group. In a preferred embodiment, Y is a heteroaliphatic or heteroaromatic ligand, a carbene ligand, a phosphine ligand or a heterocyclic ring of formula (2):

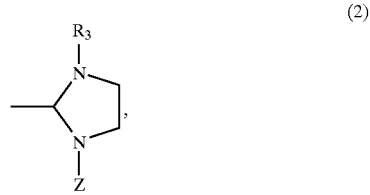

(2)

wherein: $R_3$ comprises an aromatic ring and Z comprises an aromatic or heteroaromatic ring substituent.

Z comprises an aromatic or heteroaromatic ring substituent. Z is bonded to Y and to either $R_1$ or $R_2$. In one embodiment, Z is chiral. When Z is a biaryl such as for example, a 1,1'-binaphthalene group, Z can have configurational isomers (atropisomerism) in which the chirality is determined by the sterically hindered rotation about the single bond between the two aryl rings.

In one embodiment, $R_1$ or $R_2$ are each independently a dissimilar anionic electron-withdrawing monovalent or divalent ligand. In another embodiment, $R_1$ or $R_2$ is a heteroatom. Preferably, $R_1$ or $R_2$ is oxygen (O) or sulfur (S). In another embodiment $R_1$ or $R_2$ is a halogen. Preferably $R_1$ or $R_2$ is chlorine (Cl).

In one embodiment, M is ruthenium; X is O; R is a lower alkyl group (e.g., $C_1$–$C_{12}$ linear or branched alkyl); $R_1$ is a heteroatom, preferably oxygen or sulfur; $R_2$ is a halogen atom; a, b, c and d each comprise hydrogen or a lower alkyl group (e.g., $C_1$–$C_{12}$); Y comprises a 4,5-dihydro-imidazol-2-ylidene ring or a phosphine group; and Z comprises a 1,1'-binaphthalene group.

In a preferred embodiment, M is ruthenium; X and $R_1$ are O; R is isopropyl; $R_2$ is a chlorine atom (Cl); a, b, c and d each comprise hydrogen; and Y comprises a heterocyclic ring structure having the following Formula (2):

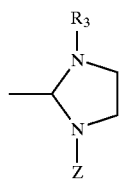

(2)

wherein $R_3$ comprises an aromatic ring group, and Z is as described above. In a currently preferred embodiment, $R_3$ comprises a 2,4,6-trimethylphenyl (mesityl) group, and Z is as described above.

BRIEF DESCRIPTION OF THE FIGURE

FIG. 1 shows a schematic illustration of the x-ray crystal structure of chiral metathesis catalyst 9 of the invention.

DETAILED DESCRIPTION OF THE INVENTION

The present invention relates to chiral metathesis catalysts for stereoselective synthesis that are both efficient and reusable. More particularly, the present invention concerns transition metal catalysts that comprise chiral ligands that are optically active or racemic. In one aspect, the chiral ligands of the invention are multidentate, and include both an aromatic and a carbene-containing group. The chiral ligands according to the present invention can be a pure enantiomer or diastereomer comprising one or more chiral centers. The chiral ligands according to the present invention can be a racemic or non-racemic mixture of enantiomers, or diastereomers. Preferably, the ligands according to the invention have an optical purity of at least about 85% ee.

The chiral catalysts of the invention are organometallic complexes comprising a transition metal that is associated with one or more multidentate chiral ligands of the invention via metal-ligand bonding. The present invention also provides methods for preparation of the chiral catalysts, and their use in catalyzing asymmetric, stereoselective olefin synthesis from alkenes.

The chiral catalysts of the invention can be chiral about the metal center, about the ligand, or both about the metal and about the ligand.

In one embodiment, the present invention provides transition metal-based complexes comprising a transition metal, for example, Mo, W, Rh, Rb, or Ru that is complexed with a multidentate chiral ligand of the invention (Formula (1)). The chiral ligand of the invention can either be a pure enantiomer, racemate or a mixture of enantiomers preferably with about 85% ee. In a preferred embodiment, the chiral ligand of the invention is a bidentate chiral ligand comprising both a carbene group and an aromatic group (Formula (2)).

In one embodiment, the chiral catalysts of the invention can be represented by the general Formula (3), wherein M is Ru, Rb, Rh, Mo, or W, and $R_4$, $R_5$ and $R_6$ are independently H, alkyl, alkoxy, aryl or heteroaryl.

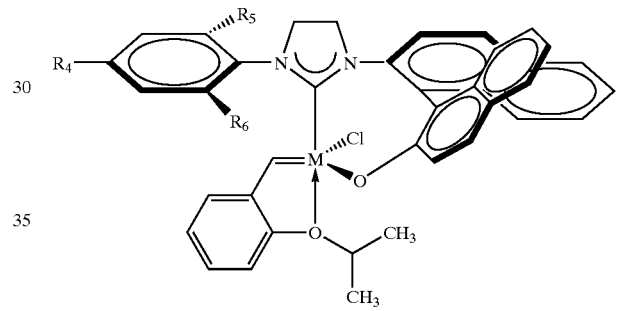

(3)

Chiral catalysts 3 of the invention bear a stereogenic metal center, and can be prepared in high diastereo- and enantiomeric purity without requiring further optical resolution, and are air-stable and recyclable. The chiral catalysts 3 efficiently promote asymmetric ring-opening/cross metathesis reactions of olefinic substrates and can be recovered from reaction mixtures by separation from products by standard separation process methods.

The chiral metathesis catalysts 3 of the invention can be synthesized by the general reaction sequence outlined in Scheme 1. The reductive amination of optically pure 1,1'-binapthyl-aminophenol 4 and aldehyde 5 in the presence of sodium triacetoxyborohydride (NaBH(OAc)$_3$) gives the corresponding amino alcohol 6. Conversion of amino alcohol 6 to imidazolinium salt 7 is accomplished in two steps. Optically pure 7 is obtained in a purified form by standard filtration. The conversion of the optically pure imidazolinium salt 7 to catalyst 3 is accomplished by reacting 7 and the catalytically inactive transition metal complex 8 (prepared by known methods in the art) in the presence of silver carbonate.

Scheme 1

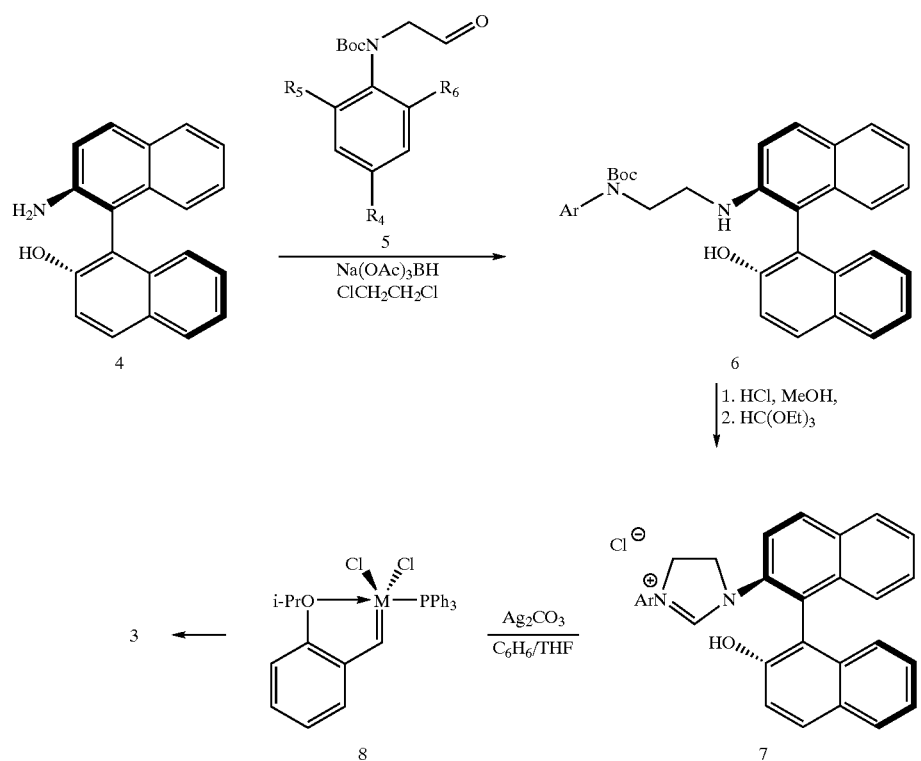

Boc = t-Butoxycarbonyl, i-Pr = isopropyl

In a preferred embodiment, the chiral catalyst of the invention comprises a Ru metal center that is complexed with a chiral ligand comprising both a carbene group and an aromatic group comprising a binapthalene ring. The chemical structure of the preferred embodiment catalyst is shown as Formula (9) below.

(9)

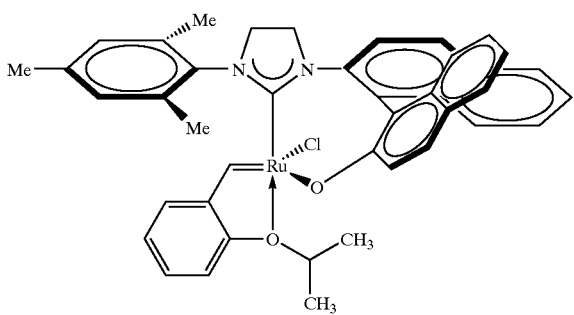

Chiral catalyst 9 bears a stereogenic Ru center, and can be prepared in >98% diastereo- and enantiomeric purity without requiring further optical resolution, and is air-stable and recyclable. The chiral catalyst 9 efficiently promotes asymmetric ring-opening/cross metathesis (AROM/CM) in air with a variety of substrates (including ones that are normally not catalyzed by previously known metal-based metathesis catalysts), and are easily recycled and reused.

The representative example synthesis of optically and diastereomerically pure 9 is shown in Scheme 2. Reductive amination involving optically pure 4 and aldehyde 11 in the presence of sodium triacetoxyborohydride (NaBH(OAc)$_3$) provided amino alcohol 12 in >98% isolated yield. Conversion of 12 to imidazolinium salt 13 involved two steps with about 83% overall yield. Optically pure 13 was then obtained in a purified form by standard filtration. The conversion of imidazolinium salt 13 to catalyst 9 was accomplished by reacting 13 and the catalytically inactive Ru complex 14 in the presence of silver carbonate. Complex 9 was formed in 52% isolated yield after silica gel chromatography.

Scheme 2

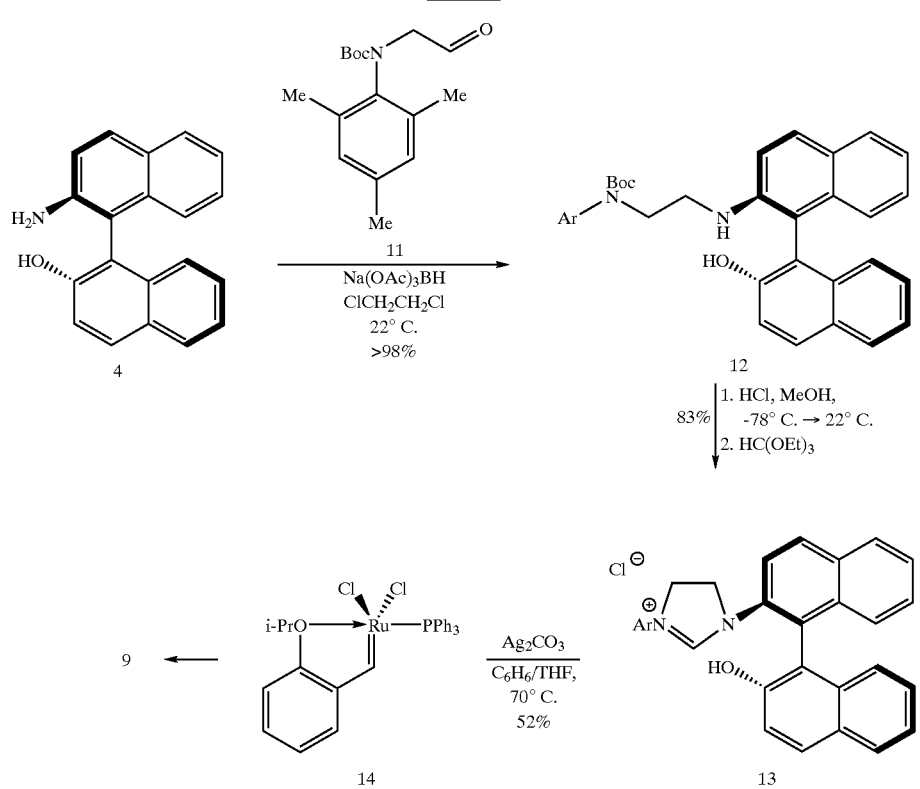

Boc = t-Butoxycarbonyl, i-Pr = isopropyl
Ar = 2,4,6-trimethylphenyl

Catalyst 9 is air-stable, can be purified by silica gel chromatography with undistilled solvents, and its diastereo- and enantiomeric purity was established by HPLC analysis (isolated in >98% de and ee respectively). The chiral complex 9 was structurally characterized by X-ray crystal structure analysis (FIG. 1).

The typical catalytic activity of the chiral metathesis catalysts of the invention is shown in the case of the representative example catalyst 9 in an olefin metathesis reaction. (Scheme 3). Chiral Ru catalyst 9 promotes the RCM of diene 15 and dienyne 17 substrates to give cyclic unsaturated products 16 and 18 bearing di- or tri-substituted olefins, respectively. Catalyst 9 can be recovered in high yield by silica gel chromatography. After its isolation, 9 can be reused without significant loss of activity. For example, the catalyst recovered from the synthesis of 16 and reused effects the RCM of 15 in an equally facile manner (about 93% conversion in 48 h) and provides the desired product in about 90% isolated yield (about 78% catalyst was recovered).

Scheme 3

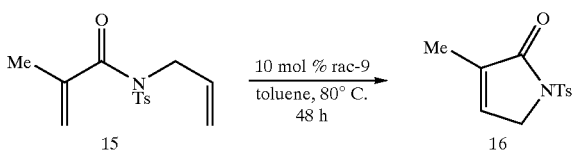

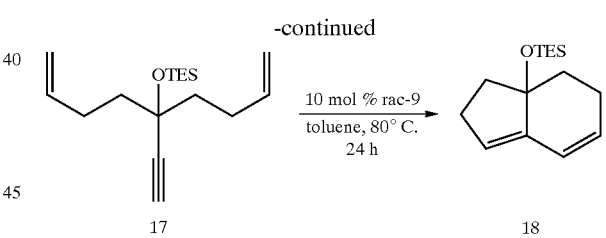

The catalysts of the invention are effective and practical chiral catalysts for enantioselective metathesis. Examples of AROM/CM reactions catalyzed by chiral catalysts of the invention are shown in Table 1. As shown in Example 1, treatment of 19 with 5 equivalents of styrene in the presence of 10 mol % catalyst 9 in THF (50° C.) leads to the formation of 20a in 80% ee and 71% isolated yield (>98% trans). Ru-catalyzed AROM/CM is highly selective with aliphatic olefins. With aliphatic olefins such as 1-heptene and sterically bulky vinylcyclohexane (entries 2–3), 20b–c are obtained in >98% ee, >98% trans and 57–60% yield.

The advantages provided by the present chiral catalysts include: (i) high post-reaction catalyst recovery after chromatography (about 88–96% yield), (ii) no observable byproducts from homodimerization of the terminal olefins or additional cross metathesis (CM) meso dienes, (iii) reuse of recovered catalysts is possible without any significant loss of enantioselectivity or catalyst reactivity; and (iv) transformations (such as those shown in Table 1) not normally effected by chiral Mo-based catalysts can be accomplished.

TABLE 1

Ru-Catalyzed AROM/CM of Tricyclic Norbornenes[a]

| en-try | R | | temp (° C.); time (h) | conv (%);[b] yield (%)[c] | recov. cat. (%)[c] | trans:cis[b] | ee (%)[d] |
|---|---|---|---|---|---|---|---|
| 1 | Ph | a | 50; 1.0 | >98; 71 | 96 | >98:2 | 80 |
| 2 | n-C$_5$H$_{11}$ | b | 50; 1.5 | >98; 57 | 92 | >98:2 | >98 |
| 3 | Cy | c | 50; 1.0 | >98; 60 | 88 | >98:2 | >98 |

[a]Conditions: 5 equiv terminal olefin in entry 1; 2 equiv in entries 2–3; THF, under N$_2$.
[b]By $^1$H NMR analysis.
[c]Isolated yields after chromatography.
[d]By chiral HPLC The stereoselectivity potential of the chiral catalysts of the invention in enantioselective catalytic AROM/CM reactions is illustrated in Scheme 4. Transformation of 21a, for example, was effected by catalysis with 5 mol % of chiral catalyst 9 at room temperature in air, using either reagent grade (undistilled, non-degassed) or purified THF to provide 22a in about 95% ee and ~66% isolated yield (>98% trans). When 0.5 mol % 9 is used, 21b reacts in 75 min to provide 22b in ~96% ee and ~76% yield (>98% trans).

Scheme 4

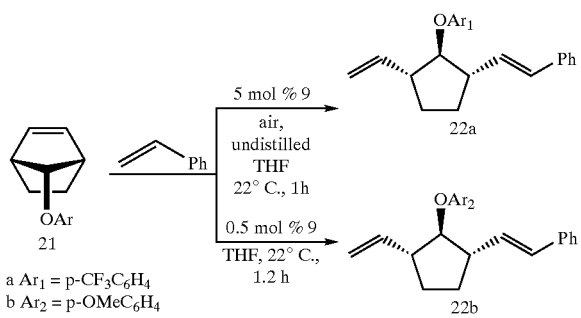

a Ar$_1$ = p-CF$_3$C$_6$H$_4$
b Ar$_2$ = p-OMeC$_6$H$_4$

Experimental Methods and Materials
General Methods

All crystalline intermediates involved in chiral ligand synthesis, including the heterocyclic and diamine hydrochloride salts, were preferably dried for about 12 h or more in a vacuum dessicator or an Abderhalden pistol containing P$_2$O$_5$. Reactions were typically carried out using distilled and degassed solvents under an atmosphere of dry nitrogen in oven—(135° C.) and flame-dried glassware with standard Schlenk or vacuum-line techniques. Infrared (IR) spectra were recorded on a Perkin-Elmer 781 spectrophotometer, and the v$_{max}$ recorded in cm$^{-1}$. Bands are characterized as broad (br), strong (s), medium (m), and weak (w). $^1$H NMR spectra were recorded on a Varian Gemini 2000 (400 MHz) spectrometer. Chemical shifts are reported in ppm from tetramethylsilane with the solvent resonance as the internal standard (CDCl$_3$: δ 7.26 ppm, (CD$_3$)$_2$SO: δ 2.50 ppm). Data are reported as follows: chemical shift, multiplicity (s=singlet, d=doublet, t=triplet, q=quartet, br=broad, m=multiplet), coupling constants (Hz), integration, and assignment. $^{13}$C NMR spectra were recorded on a Varian Gemini 2000 (100 MHz) spectrometer with complete proton decoupling. Chemical shifts are reported in ppm from tetramethylsilane with the solvent as the internal reference (CDCl$_3$: δ 77.16 ppm, (CD$_3$)$_2$SO: δ 39.52 ppm). Enantiomer ratios were determined by chiral HPLC analysis (Chiral Technologies Chiralpak AS, Chiralpak AD, and Chiralcel OD (0.46 cm×25 cm)) in comparison with authentic racemic materials. See below for further details.

Materials. Cl$_2$Ru(=CH-o-OiPrC$_6$H$_4$)PPh$_3$ (14) was prepared as previously reported (Kingsbury et al., J. Am. Chem. Soc. (1999), 121, 791). All other materials were obtained from commercial sources and purified before use. Tetrahydrofuran and toluene were distilled from sodium metal/benzophenone ketyl. CH$_2$Cl$_2$, 1,2-dichloroethane, CDCl$_3$, (CD$_3$)$_2$SO, pentane, hexanes, cyclohexane, triethylamine, ethanol, isopropanol, styrene, 1-heptene and vinylcyclohexane were distilled from calcium hydride. Methanol was distilled over Mg under nitrogen. Acetone was distilled from potassium carbonate. Dimethylformamide was stored under nitrogen over activated 4 Å molecular sieves. 2,4,6-trimethylaniline (Aldrich) was vacuum distilled. 4-Bromo-2-methyl-2-butene (Aldrich) was vacuum distilled to a colorless oil prior to use. Potassium hydride (Aldrich) was washed with pentane, dried in vacuo, and stored in a glove box. Boron tribromide (Aldrich) was vacuum distilled using a cold trap. Methyl iodide (Aldrich) and ethyl chloroformate (Aldrich) were distilled from calcium chloride. Triethylorthoformate (Aldrich) was distilled from sodium metal. cis-5-Norbornene-endo-2,3-dicarboxylic anhydride (Aldrich) was recrystallized from cyclohexane. The following materials were purchased from commercial sources and used as received: Mg turnings (Strem), di-tert-butyl dicarbonate (Advanced Chemtech), dimethyl sulfide (Aldrich), silver (I) carbonate (Strem), 2-methoxynaphthalene (Aldrich), 48% HBr (Fisher), (CH$_3$)$_2$SO (Aldrich), acetic acid (Fisher), 1-hydroxy-2-naphthoic acid (Aldrich), (1R,2S,5R)-(-)-menthol (Aldrich), 60% sodium hydride in oil (Aldrich), potassium hydroxide (Fisher), sodium triacetoxyborohydride (Aldrich), and hydrogen chloride gas (AGA).

Silica gel column chromatography was driven with compressed air and performed using silica gel 60 (230–400 mesh; pH (10% suspension) 6.5–7.0; surface area 500 m$^2$/g; pore volume 0.75 ml/g) obtained from TSI Chemical Co. (Cambridge, Mass.). Chiral catalyst 9 forms a dark brown solution in organic solvents. The progress of chromatography was followed visually as a brown-colored band on a column, and the presence of catalyst in fractions of eluant is evident by simple visual inspection. Purification and recovery following olefin metathesis was performed in air using reagent-grade solvents. Appropriate solvent mixtures for catalyst elution include the following: 4:1 hexanes:EtOAc, 3:1 hexanes:Et$_2$O, and 100% CH$_2$Cl$_2$ (R$_f$ values ~0.15–0.30). For polar reaction products the reaction mixture was passed through a short plug of silica gel in CH$_2$Cl$_2$ to separate the catalyst from reaction products, with recourse to a second column chromatographic separation of the organic materials.

Synthetic methods for racemic 4 was accomplished via a diastereoselective biaryl coupling reaction using (1R,2S, 5R)-(−)-menthol as a chiral auxiliary.

The invention is illustrated by the following examples, which are not intended to be limiting in any way.

EXAMPLES

Example 1

1-Bromo-2-methoxynaphthalene. Prepared according to a literature procedure. Majetich, G.; Hicks, R.; Reister, S., *J. Org. Chem.* (1997), 62, 4321–4326. IR (NaCl): 3047 (w), 2972 (m), 2943 (m), 2843 (m), 1622 (s), 1596 (m), 1501 (s), 1467 (m), 1454 (m), 14.40 (w), 1353 (m), 1335 (m), 1271 (s), 1247 (w), 1219 (m), 1187 (m), 1173 (w), 1153 (w), 1064 (s), 1023 (m), 892 (m), 840 (m), 813 (m), 803 (s), 763 (m), 743 (s), 518 (m). $^1$H NMR (400 MHz, CDCl$_3$): δ 8.19 (d, J=8.6 Hz, 1H), 7.75 (t, J=8.5 Hz, 2H), 7.53 (t, J=8.2 Hz, 1H), 7.36 (t, J=7.9 Hz, 1H), 7.22 (d, J=9.0 Hz, 1H), 3.98 (s, 3H). $^{13}$C NMR (100 MHz, CDCl$_3$): δ 153.88, 133.25, 130.94, 129.09, 128.16, 127.86, 126.24, 124.43, 113.74, 108.78, 57.17. HRMS Calcd for C$_{11}$H$_9$BrO: 235.9837. Found: 235.9838. Anal. Calcd for C$_{11}$H$_9$BrO: C, 55.72; H, 3.83. Found: C, 55.66; H, 3.82.

Example 2

Methyl 1-methoxynaphthoate. Prepared according to the procedures described in Hattori, T.; Hotta, H.; Suzuki, T.; Miyano, S. *Bull. Chem. Soc. Jpn.* (1993), 66, 613–622. IR (NaCl): 3058 (w), 2997 (w), 2948 (m), 2846 (w), 1725 (s), 1628 (m), 1597 (m), 1570 (m), 1504 (m), 1466 (m), 1445 (m), 1434 (m), 1373 (s), 1343 (s), 1279 (s), 1239 (s), 1214 (m), 1191 (m), 1153 (m), 1133 (s), 1084 (s), 1001 (m), 829 (m), 802 (m), 787 (m), 768 (s), 715 (w). $^1$H NMR (400 MHz, CDCl$_3$): δ 8.30–8.26 (m, 1H), 7.87–7.84 (m, 2H), 7.62 (d, J=8.6 Hz, 1H), 7.61–7.54 (m, 2H), 4.07 (s, 3H), 3.99 (s, 3H). $^{13}$C NMR (100 MHz, CDCl$_3$): δ 166.85, 158.44, 136.93, 128.47, 128.02, 126.83, 126.68, 123.78, 123.77, 119.34, 63.56, 52.41. HRMS Calcd for C$_{13}$H$_{12}$O$_3$: 216.0786. Found: 216.0787. Anal. Calcd for C$_{13}$H$_{12}$O$_3$: C, 72.21; H, 5.59. Found: C, 72.50; H, 5.52.

Example 3

(−)-Menthyl 1-(−)-menthyloxy-2-naphthoate was prepared by the method described by Hattori et al., *Bull. Chem. Soc. Jpn.* (1993), 66, 613. IR (NaCl): 3058 (w), 2954 (s), 2956 (s), 2869 (m), 1719 (s), 1625 (w), 1598 (w), 1568 (w), 1502 (w), 1457 (m), 1387 (m), 1371 (m), 1342 (m), 1319 (m), 1277 (s), 1235 (s), 1215 (m), 1203 (m), 1181 (w), 1148 (s), 1137 (s), 1098 (m), 1081 (s), 1038 (w), 1007 (w), 983 (m), 962 (m), 920 (w), 823 (w), 801 (w), 766 (m), 741 (w). $^1$H NMR ((400 MHz, CDCl$_3$): δ 8.32 (d, J=8.5 Hz, 1H), 7.81 (d, J=7.7 Hz, 1H), 7.67 (d, J=8.6 Hz, 1H), 7.56–7.48 (m, 3H), 5.04 (td, J=10.9, 4.4 Hz, 1H), 4.34 (td, J=10.9, 4.2 Hz, 1H), 2.67 (quintetd, J=6.8, 2.2 Hz, 1H), 2.21–2.16 (m, 1H), 2.05 (quintetd, J=7.2, 2.7 Hz, 1H), 1.79–1.52 (m, 7H), 1.28–0.83 (m, 23H), 0.74 (d, J=6.6 Hz, 3H). $^{13}$C NMR (100 MHz, CDCl$_3$): δ 166.77, 154.10, 136.24, 130.12, 127.86, 127.74, 126.22, 126.00, 124.56, 122.40, 121.15, 82.11, 74.59, 49.64, 47.27, 41.17, 39.97, 34.59, 34.46, 31.67, 31.61, 26.38, 25.82, 23.50, 23.42, 22.24, 22.22, 21.60, 21.04, 16.77, 16.56. HRMS Calcd for C$_{31}$H$_{44}$O$_3$: 464.3290. Found: 464.3290. Anal. Calcd for C$_{13}$H$_{44}$O$_3$: C, 80.13; H, 9.54. Found: C, 80.22; H, 9.63.

Example 4

(−)-Menthyl(S)-2'-methoxy-1,1'-binaphthalene-2-carboxylate. Mg turnings (1.30 g, 58.2 mmol) were suspended in 5 mL of THF in a 100 mL round bottom flask and treated with a solution of 1-bromo-2-methoxynaphthylene (4.60 g, 19.4 mmol in 20 mL of THF) using a cannula. This mixture was stirred at reflux for 1.5 h. Benzene (25 mL) was then added and the mixture was transferred through a cannula into a solution of (−)-menthyl 1-(−)-menthyloxy-2-naphthoate (7.64 g, 16.4 mmol in 15 mL of benzene) at 0° C. The ice bath was removed and the resulting solution was stirred at 22° C. for 3 days. The mixture was then quenched by the addition of 50 mL of a saturated ammonium chloride solution. The mixture was diluted with 100 mL of water and 100 mL of benzene and transferred to a separatory funnel. The organic layer was washed with one volume each of water and a saturated sodium chloride solution. The solution was then dried over MgSO$_4$, filtered, and concentrated to a thick yellow oil. Purification by silica gel chromatography in 20:1 hexanes:Et$_2$O (R$_f$=0.15) on a column 10 cm in diameter and 20 cm in length delivered a bright white solid (5.95 g, 12.8 mmol, 78%). IR (NaCl): 3059 (m), 3003 (w), 2954 (s), 2933 (s), 2868 (s), 1721 (s), 1697 (s), 1622 (m), 1294 (s), 1510 (s), 1461 (s), 1433 (m), 1367 (m), 1336 (s), 1321 (s), 1271 (s), 1250 (s), 1213 (w), 1180 (m), 1147 (s), 1136 (s), 1127 (s), 1084 (s), 1054 (m), 1038 (w), 1021 (m), 1008 (w), 982 (m), 963 (m), 907 (w), 869 (w), 832 (m), 808 (s), 788 (w), 768 (s), 738 (s), 704 (w). $^1$H NMR (400 MHz, CDCl$_3$): δ 8.14 (d, J=8.6 Hz, 1H), 7.99 (m, 2H), 7.94 (d, J=8.1 Hz, 1H), 7.85 (d, J=8.2 Hz, 1H), 7.53 (t, J=7.5 Hz, 1H), 7.42 (d, J=9.0 Hz, 1H), 7.36 (d, J=8.4 Hz, 1H), 7.29 (t, J=7.8 Hz, 2H), 7.17 (dd, J=8.4, 7.2 Hz, 1H), 6.97 (d, J=8.4 Hz, 1H), 4.49 (td, J=10.8, 4.4 Hz, 1H), 3.75 (s, 3H), 1.55–1.15 (m, 5H), 0.91–0.48 (m, 11H), −0.21 (q, J=12.3 Hz, 1H). $^{13}$C NMR (100 MHz, CDCl$_3$): δ167.60, 154.32, 136.60, 135.19, 134.31, 133.07, 129.94, 129.38, 129.14, 128.10, 127.98, 127.83, 127.63, 126.66, 126.62, 126.62, 126.52, 124.97, 123.58, 122.40, 113.29, 74.41, 56.51, 46.68, 39.67, 34.19, 31.11, 25.65, 22.90, 21.98, 21.06, 15.82. HRMS Calcd for C$_{32}$H$_{34}$O$_3$: 466.2508. Found: 466.2508. Anal. Calcd for C$_{32}$H$_{34}$O$_3$: C, 82.37; H, 7.34. Found: C, 82.13; H, 7.30.

Example 5

(S)-2'-Methoxy-1,1'-binaphthalene-2-carboxylic acid. A solution of KOH (18.7 g, 333 mmol, 20 equiv) in absolute ethanol (167 mL) was poured through a funnel into a 500 mL round bottom flask containing (−)-menthyl-(S)-2'-methoxy-1,1'-binaphthalene-2-carboxylate (7.80 g, 16.7 mmol). The flask was equipped with a reflux condenser and purged with nitrogen. As heat was applied from a heating mantle the sparingly soluble ester gradually dissolved, forming a light yellow solution. This solution was stirred at reflux for 24 h, at which point TLC analysis of the reaction mixture indicated an absence of starting material. The reaction mixture was cooled to 22° C. and concentrated to a volume <15 mL. This solution was diluted with 250 mL of water and washed three times with 200 mL portions of Et$_2$O (these organic layers were discarded). The aqueous layer was then acidified to pH<2 using concentrated hydrochloric acid, resulting in a voluminous deposition of a cloudy white precipitate. This solid was extracted from the aqueous layer with three 200 mL volumes of Et$_2$O. These organic layers were combined, dried over MgSO$_4$, and filtered. Concentration of the resulting solution gave the acid of >98% purity as a light yellow crystalline solid (5.43 g, >98% yield). IR (NaCl): 3059 (br), 3013 (br), 2935 (w), 2898 (w), 2838 (m), 2635 (br), 2564

(br), 1691 (s), 1621 (m), 1593 (m), 1566 (w), 1508 (m), 1464 (m), 1432 (w), 1408 (w), 1360 (w), 1332 (w), 1288 (m), 1263 (s), 1249 (s), 1178 (w), 1145 (m), 1130 (w), 1084 (m), 1054 (w), 1020 (w), 956 (w), 908 (w), 835 (w), 806 (m), 772 (m), 752 (m), 735 (m). $^1$H NMR (400 MHz, CDCl$_3$): δ 9.60 (br, 1H, COOH), 8.15 (d, J=8.8 Hz, 1H, aromatic H), 8.01–7.97 (m, 2H, aromatic H), 7.94 (d, J=8.4 Hz, 1H, aromatic H), 7.89 (d, J=8.2 Hz, 1H, aromatic H), 7.54 (m, 1H, aromatic H), 7.37 (d, J=9.2 Hz, 1H, aromatic H), 7.33–7.21 (m, 3H, aromatic H), 7.17 (dd, J=7.5, 7.5 Hz, 1H, aromatic H), 6.89 (d, J=8.6 Hz, 1H, aromatic H), 3.68 (s, 3H, ArOCH$_3$). $^{13}$C NMR (100 MHz, CDCl$_3$): δ 154.30, 138.21, 135.65, 133.89, 133.07, 129.72, 129.07, 128.14, 128.09, 128.04, 127.88, 126.85, 126.61, 124.94, 123.61, 121.59, 113.74, 56.72. HRMS Calcd for C$_{22}$H$_{16}$O$_3$: 328.1099. Found: 328.1098. Anal. Calcd for C$_{22}$H$_{16}$O$_3$: C, 80.47; H, 4.91. Found: C, 80.24; H, 4.96.

Example 6

(S)-2-Amino-2'-methoxy-1,1'-binaphthalene. A 250 mL round bottom flask was charged with (S)-2'-methoxy-1,1'-binaphthalene-2-carboxylic acid (5.43 g, 16.5 mmol), 83 mL of acetone, and Et$_3$N (2.53 mL, 18.2 mmol, 1.10 equiv), and the resulting solution was cooled to −15° C. (CO$_2$/ethylene glycol bath). The subsequent dropwise addition of ethyl chloroformate (1.89 mL, 19.8 mmol, 1.20 equiv) caused a cloudy white precipitate to form. This suspension was stirred for 30 min at −15° C., at which time a solution of NaN$_3$ (3.22 g, 49.5 mmol, 3.0 equiv) in 16 mL of water was added. After stirring for an additional 90 min at −15° C., the reaction mixture was diluted with 150 mL of water and washed three times with 125 mL of cold benzene. The combined organic layers were washed with 400 mL of a cold saturated sodium chloride solution, dried over MgSO$_4$, and filtered directly into a 500 mL round bottom flask containing 1.0 g of activated 4 Å molecular sieves. This vessel was equipped with a reflux condenser and heating mantle and the bronze-colored solution was heated at reflux for 2 h. After cooling to 22° C., the solution was filtered into another 500 mL round bottom flask containing a solution of KOH (46.3 g, 825 mmol, 50 equiv) in 85 mL of water. The resulting biphasic mixture was stirred vigorously for 16 h and transferred to a separatory funnel. The organic layer was isolated and the aqueous layer was washed two times with 100 mL of benzene. This solution was dried (MgSO$_4$), filtered, concentrated to afford a light yellow solid of >95% purity as judged by $^1$H NMR analysis. This material was typically purified further before use. After dissolving the solid in 20–25 mL of CH$_2$Cl$_2$, 8–10 g of silica gel was added and the solvent was removed from the slurry under reduced pressure. The product-laden silica gel was loaded onto a wide plug of silica gel and eluted with 1:1 hexanes:Et$_2$O (R$_f$= 0.30). The title product was obtained in excellent yield as a bright white solid (4.74 g, 96%). Alternatively, the unpurified product was recrystallized as a white solid from absolute ethanol (3.95 g, 80%). IR (NaCl): 3483 (br), 3384 (m), 3056 (w), 3004 (w), 2964 (w), 2939 (w), 2838 (w), 1619 (s), 1591 (m), 1506 (s), 1474 (w), 1463 (m), 1431 (m), 1381 (m), 1352 (w), 1330 (w), 1261 (s), 1246 (s), 1213 (w), 1178 (w), 1146 (m), 1132 (w), 1111 (w), 1076 (m), 1048 (w), 1019 (w), 903 (w), 811 (s), 781 (w), 775 (w), 749 (m), 736 (m), 707 (w). $^1$H NMR (400 MHz, CDCl$_3$): δ 8.00 (d, J=9.0 Hz, 1H, aromatic H), 7.89 (d, J=8.2 Hz, 1H, aromatic H), 7.81–7.77 (m, 2H, aromatic H), 7.48 (d, J=9.0 Hz, 1H, aromatic H), 7.35 (m, 1H, aromatic H), 7.28–7.13 (m, 4H, aromatic H), 7.14 (d, J=8.6 Hz, 1H, aromatic H), 6.99–6.96 (m, 1H, aromatic H), 3.79 (s, 3H, ArOCH$_3$), 3.57 (s, 2H, ArNH$_2$). $^{13}$C NMR (100 MHz, CDCl$_3$): δ 155.59, 142.03, 134.30, 133.76, 130.13, 129.72, 129.14, 128.38, 128.19, 128.14, 127.04, 126.42, 125.15, 124.43, 124.06, 122.29, 119.00, 118.35, 114.49, 114.05, 57.01. HRMS Calcd for C$_{21}$H$_{17}$NO: 299.1310. Found: 299.1310. Anal. Calcd for C$_{21}$H$_{17}$NO: C, 84.25; H, 5.72; N, 4.68. Found: C, 84.07; H, 5.77; N, 4.68. [α]$_D^{25}$ −67.11° (c=1.041, CHCl$_3$).

Example 7

(S)-2-Amino-2'-hydroxy-1,1'-binaphthalene (NOBIN) (10). (S)-2-Amino-2'-methoxy-1,1'-binaphthalene (4.30 g, 14.4 mmol) was dissolved in 144 mL of CH$_2$Cl$_2$ in a 250 mL round bottom flask and the colorless solution was cooled to 0° C. Boron tribromide (BBr$_3$) (5.44 mL, 57.5 mmol, 4.0 equiv) was then added dropwise using a syringe, at which point the solution turned slightly yellow in color. The reaction mixture was warmed to 22° C. and stirred for 12 h, at which point a small aliquot worked up as described below to confirm the absence of starting material ($^1$H NMR analysis). The reaction mixture was cooled to 0° C. and carefully poured into a 1 L separatory funnel containing 100 mL of 5 M NaOH. After quenching of excess BBr$_3$, the mixture was diluted with 200 mL of water and 200 mL of EtOAc. The organic layer was removed, and the aqueous layer was washed two times with 100 mL of EtOAc. The combined organic layers were dried over MgSO$_4$, filtered, and concentrated to an off-white solid of >95% purity as judged by $^1$H NMR analysis. This material was purified further prior to reductive amination. After dissolution of the solid in minimal 1:1 EtOAc:CH$_2$Cl$_2$ (approximately 50–60 mL), 25 g of silica gel was added, following which the solvent was removed from the slurry under reduced pressure. The product-laden silica gel was loaded onto a wide plug of silica gel and eluted with 3:1 hexanes:EtOAc (R$_f$= 0.29). This procedure delivered the product as a white solid (3.34 g, 96%). Alternatively, the unpurified product was also recrystallized as an off-white solid from absolute ethanol (3.07 g, 75%). IR (NaCl): 3396 (m), 3323 (m), 3300 (br), 3057 (w), 1616 (s), 1594 (s), 1508 (m), 1471 (w), 1461 (w), 1381 (s), 1344 (w), 1273 (w), 1214 (m), 1168 (m), 1142 (m), 1128 (m), 910 (w), 820 (s), 775 (w), 752 (w), 727 (s). $^1$H NMR (400 MHz, CDCl$_3$): δ 7.93 (d, J=9.0 Hz, 1H, aromatic H), 7.90–7.84 (m, 2H, aromatic H), 7.82–7.79 (m, 1H, aromatic H), 7.38 (d, J=9.0 Hz, 1H, aromatic H), 7.35 (ddd, J=8.0, 6.8, 1.5 Hz, 1H, aromatic H), 7.30–7.16 (m, 4H, aromatic H), 7.15 (d, J=8.8 Hz, 1H, aromatic H), 7.07–7.03 (m, 1H, aromatic H), 5.13 (s, 1H, ArOH), 3.74 (s, 2H, ArNH$_2$). $^{13}$C NMR (100 MHz, CDCl$_3$): δ 151.97, 143.90, 134.27, 133.34, 130.78, 130.51, 129.67, 128.52, 128.46, 128.40, 127.47, 127.11, 124.69, 123.88, 123.80, 122.91, 118.31, 117.84, 114.42, 108.62. HRMS Calcd for C$_{20}$H$_{15}$NO: 285.1154. Found: 285.1154. Anal. Calcd for C$_{20}$H$_{15}$NO: C, 84.19; H, 5.30; N, 4.91. Found: C, 83.97; H, 5.18; N, 4.84. [α]$_D^{25}$ −56.38° (c=1.002, CHCl$_3$).

Example 8

N-(tert-Butyloxycarbonyl)-2,4,6-trimethylphenylamine. A 100 mL round bottom flask was charged with 2,4,6-trimethylaniline (3.59 g, 26.6 mmol) and 20 mL of THF. Di-tert-butyl dicarbonate (5.81 g, 26.6 mmol, 1.0 equiv) was weighed into a 25 mL pear-shaped flask and dissolved in 30 mL of THF. The anhydride was then transferred to the arylamine solution through a cannula. A 3 mL portion of THF was used to complete the transfer (final concentration 0.5 M). The reaction flask was equipped with a reflux condenser and heating mantle, and the resulting colorless solution was heated at reflux for 7 days. At this time, a $^1$H NMR spectrum of the reaction mixture was obtained to confirm finally revealed an absence of the starting aniline. Solvent removal in vacuo provided the product in optimally >98% purity as an off-white crystalline solid (6.25 g, >98%), the product was additionally purified by silica gel chromatography in 8:1 hexanes:Et$_2$O (R$_f$=0.20). Though UV active, the product is detectable with a ninhydrin TLC stain. IR (NaCl): 3303 (br), 3004 (w), 2978 (m), 2922 (m), 2862 (w), 1698 (s), 1611 (w), 1507 (s), 1458 (m), 1391 (m), 1366 (s), 1308 (w), 1248 (s), 1171 (s), 1055 (m), 1022 (m), 904 (w), 849 (m), 777 (w), 707 (w). $^1$H NMR (400 MHz, CDCl$_3$): δ 6.88 (s, 2H, aromatic H), 5.89 (br, 1H, ArNH), 2.27 (s, 3H, p-CH$_3$), 2.23 (s, 6H, o-CH$_3$), 1.52 (br, 9H, OC(CH$_3$)$_3$). $^{13}$C NMR (100 MHz, CDCl$_3$): δ 153.95, 136.45, 135.63, 131.48, 128.85, 79.69, 28.40, 20.95, 18.31. HRMS Calcd for C$_{14}$H$_{21}$NO$_2$: 235.1572. Found: 235.1567. Anal. Calcd for C$_{14}$H$_{21}$NO$_2$: C, 71.46; H, 8.99. Found: C, 71.56; H, 8.76.

Example 9

N-(tert-Butyloxycarbonyl)-N-(3-methyl-but-2-enyl)-2,4,6-trimethylphenylamine. A suspension of KH (1.27 g, 31.7 mmol, 1.10 equiv) in 20 mL of DMF in a 100 mL round bottom flask was cooled to 0° C. The aryl carbonate (6.67 g, 28.7 mmol, 1.0 equiv) was dissolved in DMF (40 mL) and added to the mixture dropwise through a cannula, causing vigorous gas evolution. The resulting mixture was warmed to 22° C. and stirred for 1 h. 4-Bromo-2-methyl-2-butene (3.98 mL, 34.5 mmol, 1.20 equiv) was next added dropwise from a syringe, inducing a rapid precipitation of white KBr salts. After 1 h of additional stirring at 22° C., the mixture was transferred to a separatory funnel and diluted with 100 mL of a saturated sodium bicarbonate solution, 100 mL of H$_2$O, and 200 mL of Et$_2$O. The organic layer was removed and the aqueous layer was washed with two 150 mL portions of Et$_2$O. The combined organic layers were washed with one volume of a saturated sodium chloride solution. The resulting solution was dried over MgSO$_4$, filtered, and concentrated to a bronze oil of >95% purity as judged by $^1$H NMR analysis. This material can be further purified before oxidative cleavage. This was achieved by silica gel chromatography in 10:1 hexanes:Et$_2$O (R$_f$=0.32), affording the olefin as a colorless oil (7.85 g, 90% yield). In CDCl$_3$ at 22° C., this material exists as a 2.4:1 mixture of amide rotamers. The $^1$H NMR and $^{13}$C NMR data given below indentifying each isomer in the mixture. IR (NaCl): 2975 (m), 2925 (m), 2861 (w), 1698 (s), 1483 (m), 1452 (m), 1390 (s), 1365 (m), 1329 (w), 1305 (m), 1290 (m), 1255 (m), 1239 (w), 1172 (s), 1136 (m), 1043 (w), 1000 (w), 870 (w), 851 (w), 770 (w). $^1$H NMR (400 MHz, CDCl$_3$): δ 6.84 (s, 2H, aromatic H), 6.81 (s, 2H, aromatic H), 5.30 (m, 1H, olefinic H), 4.04 (d, J=7.2 Hz, 2H, NCH$_2$), 3.97 (d, J=7.2 Hz, 2H, NCH$_2$), 2.25 (s, 6H, o-CH$_3$), 2.23 (s, 3H, p-CH$_3$), 2.16 (s, 3H, p-CH$_3$), 2.13 (s, 6H, o-CH$_3$), 1.66 (s, 3H, CHC(CH$_3$)$_2$), 1.63 (s, 3H, CHC (CH$_3$)$_2$), 1.51 (s, 9H, OC(CH$_3$)$_3$), 1.46 (s, 3H, CHC(CH$_3$)$_2$), 1.42 (s, 3H, CHC(CH$_3$)$_2$), 1.32 (s, 9H, OC(CH$_3$)$_3$). $^{13}$C NMR (100 MHz, CDCl$_3$): δ 155.07, 154.31, 137.91, 137.57, 136.64, 136.27, 136.01, 135.69, 135.22, 134.48, 129.21, 128.78, 120.96, 120.22, 79.68, 79.13, 47.67, 46.50, 28.61, 28.45, 25.81, 25.76, 21.06, 18.33, 18.25, 17.71, 17.59. HRMS Calcd for C$_{19}$H$_{29}$NO$_2$: 303.2198. Found: 303.2201. Anal. Calcd for C$_{19}$H$_{29}$NO$_2$: C, 75.21; H, 9.63; N, 4.62. Found: C, 75.50; H, 9.76; N, 4.55.

Example 10

N-(tert-Butyloxycarbonyl)-N-(formylmethyl)-2,4,6-trimethylphenylamine. The olefin (6.07 g, 20.0 mmol, 1.0 equiv) from Example 10 was dissolved in 150 mL of CH$_2$Cl$_2$ and 50 mL of methanol (3:1 ratio, 0.1 M). Sodium bicarbonate was then added to the solution directly as a solid, forming a white suspension. The flask was fitted with a plastic cap punctured with both a (12 inch) 16 gage syringe needle and a smaller needle for gas release. The flask was cooled to −78° C. and ozone was bubbled into the reaction mixture through the syringe needle until TLC analysis indicated that no starting material remained (typically 10–15 minutes). The reaction mixture was then warmed to 22° C. and reduced with dimethyl sulfide (2.90 mL, 39.5 mmol, 2.0 equiv). Solvents and excess dimethyl sulfide were then removed under high vacuum. Silica gel chromatography of the resulting oily residue in 5:1 hexane:EtOAc (R$_f$=0.35) on a short (product streaks), wide column (12 cm high; 10 cm diameter) delivered the desired aldehyde in good yield as a colorless, viscous oil (4.55 g, 82%). UV detection of this material on TLC plates is difficult, but it stains readily using ninhydrin. In CDCl$_3$ at 22° C., this material exists as a 1.6:1 mixture of amide rotamers. The $^1$H NMR and $^{13}$C NMR data given below report each resonance in the mixture. IR (NaCl): 3450 (br), 3369 (br), 2977 (s), 2923 (s), 2863 (m), 2820 (m), 2720 (w), 1737 (s), 1693 (s), 1610 (w), 1486 (s), 1455 (s), 1423 (s), 1368 (s), 1342 (m), 1319 (s), 1302 (s), 1277 (m), 1255 (s), 1224 (s), 1168 (s), 1151 (s), 1068 (m), 1038 (m), 988 (m), 951 (w), 913 (w), 874 (w), 854 (m), 816 (w), 773 (m), 733 (w), 675 (w), 625 (w), 601 (w), 585 (w). $^1$H NMR (400 MHz, CDCl$_3$): δ 9.81 (m, 1H, CHO), 6.89 (d, J=0.4 Hz, 2H, aromatic H), 6.87 (d, J=0.6 Hz, 2H, aromatic H), 3.96 (d, J=1.6 Hz, 2H, NCH$_2$), 3.95 (d, J=1.4 Hz, 2H, NCH$_2$), 2.27 (s, 6H, o-CH$_3$), 2.25 (s, 3H, p-CH$_3$), 2.23 (s, 3H, p-CH$_3$), 2.21 (s, 6H, o-CH$_3$), 1.49 (s, 9H, OC(CH$_3$)$_3$), 1.36 (s, 9H, OC(CH$_3$)$_3$). $^{13}$C NMR (100 MHz, CDCl$_3$): δ 198.87, 198.83, 155.54, 153.67, 137.83, 137.68, 137.64, 137.33, 135.66, 135.25, 129.58, 129.26, 81.59, 80.75, 59.79, 59.22, 28.28, 28.23, 20.99, 18.32, 18.25. HRMS Calcd for C$_{16}$H$_{23}$NO$_3$: 277.1678. Found: 277.1679. Anal. Calcd for C$_{16}$H$_{23}$NO$_3$: C, 69.29; H, 8.36; N, 5.05. Found: C, 69.44; H, 8.31; N, 5.01.

Example 11

Diamine (12). (S)-2-Amino-2'-hydroxy-1,1'-binaphthalene (NOBIN) (10) (1.004 g, 3.519 mmol, 1.0 equiv) and sodium triacetoxyborohydride (1.492 g, 7.038 mmol, 2.0 equiv) were added as solids to a 100 mL round bottom flask and suspended in 30 mL of 1,2-dichloroethane. A solution of the aldehyde (976 mg, 3.25 mmol, 1.0 equiv) in 10 mL 1,2-dichloroethane was then introduced dropwise over a period of 1 h from a gas-tight syringe. As the reaction proceeded, the solids gradually dissolved. After 30 min of additional stirring, the reaction mixture was almost homogeneous and TLC analysis showed only a minor amount of unreacted NOBIN (10). The reaction may be completion by slowly adding additional aldehyde to the mixture (typically 0.5 more equiv). Upon complete consumption of NOBIN (10) by TLC, the reaction mixture was diluted with 100 mL of sodium bicarbonate and 50 mL of CH$_2$Cl$_2$. The organic layer was removed, and the aqueous layer was washed twice with 100 mL of CH$_2$Cl$_2$. The combined organic layers were dried over MgSO$_4$, filtered, and concentrated. Purification by silica gel chromatography in 7:3 hexanes:Et$_2$O (R$_f$=0.25) gave the protected diamine in high yield as a white foam (1.85 g, 96%). In CDCl$_3$ at 22° C., this material is present as a 2.7:1 mixture of amide rotamers. The $^1$H NMR and $^{13}$C NMR data given below report each resonance in the mixture. IR (NaCl): 3508 (m), 3470 (m), 3394 (br), 3055 (m), 2977 (s), 2927 (s), 2861 (m), 1737 (m), 1693 (s), 1619 (s), 1598 (s), 1573 (w), 1513 (s), 1494 (s), 1464 (m), 1455 (m), 1428 (m), 1393 (s), 1378 (s), 1367 (s), 1344 (m), 1311 (m), 1294 (m), 1268 (m), 1251 (m), 1217 (m), 1203 (m), 1174 (s), 1150 (s), 1080 (w), 1037 (w), 1026 (w), 1008 (w), 985 (w), 974 (w), 855 (m), 816 (m), 773 (m), 747 (m), 703 (w). $^1$H NMR (400 MHz, CDCl$_3$): δ 7.94–7.89 (m, 2H, aromatic H), 7.87–7.84 (m, 1H, aromatic H), 7.82–7.77 (m, 1H, aromatic H), 7.35 (d, J=9.2 Hz, 1H, aromatic H), 7.35–7.29 (m, 1H, aromatic H), 7.30 (d, J=8.8 Hz, 1H, aromatic H), 7.25–7.15 (m, 3H, aromatic H), 7.11–7.07 (m, 1H, aromatic H), 6.96–6.92 (m, 1H, aromatic H), 6.83–6.77 (m, 1H, aromatic H), 5.12 (s, 1H, ArOH), 5.06 (s, 1H, ArOH), 4.09 (br, 1H, ArNH), 3.78 (br, 1H, ArNH), 3.61–3.50 (m, 1H, ArNHCH$_2$), 3.45–3.33 (m, 3H, ArNHCH$_2$), 2.24 (s, 3H, p-CH$_3$), 2.22 (s, 3H, p-CH$_3$), 2.09 (s, 3H, o-CH$_3$), 2.07 (s, 3H, o-CH$_3$), 2.05 (s, 3H, o-CH$_3$), 2.03 (s, 3H, o-CH$_3$), 1.51 (s, 9H, OC(CH$_3$)$_3$), 1.23 (s, 9H, OC(CH$_3$)$_3$). $^{13}$C NMR (100 MHz, CDCl$_3$): δ 155.39, 154.15, 152.13, 144.99, 144.78, 137.48, 137.39, 137.06, 136.60, 135.70, 135.60, 135.34, 135.20, 134.33, 134.30, 133.54, 133.40, 131.01, 130.82, 130.59, 130.40, 129.69, 129.50, 129.10, 129.08, 128.46, 128.41, 128.29, 127.73, 127.59, 127.44, 127.21, 127.06, 126.88, 124.65, 124.51, 123.80, 123.64, 123.61, 122.50, 122.16, 117.83, 117.78, 114.16, 113.95, 113.62, 113.56, 108.32, 107.98, 80.55, 79.68, 49.75, 49.04, 42.40, 42.37, 28.58, 28.28, 20.99, 18.13, 18.09, 18.02, 17.99, 15.39. HRMS Calcd for C$_{36}$H$_{38}$N$_2$O$_3$: 546.2882. Found: 546.2882. Anal. Calcd for C$_{36}$H$_{38}$N$_2$O$_3$: C, 79.09; H, 7.01; N, 5.12. Found: C, 78.90; H, 7.26; N, 4.94.

Example 12

Imidazolinium chloride (13). The monoprotected diamine 12 (225 mg, 0.412 mmol) was dissolved in 4.5 mL of anhydrous methanol in a 10 mL round bottom flask and the resulting colorless solution was cooled to −78° C. Anhydrous HCl was gently bubbled through the solution for 5 min. The reaction was then allowed to warm to 22° C. and the solvent was removed at reduced pressure. The product was obtained with >98% purity ($^1$H NMR analysis) as an off-white cystalline solid (214 mg, >98%) which was rigorously dried (12 h) under vacuum in an Abderhalden pistol containing P$_2$O$_5$ over refluxing isopropanol. IR (KBr): 3396 (s), 3054 (s), 2956 (s), 2731 (s), 2363 (w), 1690 (w), 1619 (s), 1597 (s), 1511 (s), 1484 (m), 1431 (s), 1342 (m), 1272 (m), 1210 (m), 1148 (m), 1025 (w), 975 (w), 857 (w), 877 (s), 749 (s), 576 (w), 424 (w). $^1$H NMR (400 MHz, (CD$_3$)$_2$SO): δ 9.41 (br, 1H, ArOH), 7.94–7.85 (m, 3H, aromatic H), 7.80 (d, J=8.1 Hz, 1H, aromatic H), 7.39 (d, J=9.0 Hz, 2H, aromatic H), 7.26 (dd, J=7.6, 7.5 Hz, 1H, aromatic H), 7.19–7.07 (m, 3H, aromatic H), 6.93 (s, 2H, mesityl aromatic H), 6.88 (d, J=8.4 Hz, 1H, aromatic H), 6.72 (d, J=8.4 Hz, 1H, aromatic H), 4.07 (br, 4H, ArNH$_2$R), 3.78–3.70 (m, 1H, ArNH$_2$CH$_2$), 3.66–3.57 (m, 1H, ArNH$_2$CH$_2$), 3.25–3.37 (m, 2H, ArNH$_2$CH$_2$), 2.31 (s, 6H, o-CH$_3$), 2.20 (s, 3H, p-CH$_3$). $^{13}$C NMR (100 MHz, (CD$_3$)$_2$SO): δ 153.56, 143.12, 138.32, 133.90, 133.73, 131.71, 130.71, 130.31, 129.38, 128.78, 128.49, 128.06, 127.86, 127.21, 126.18, 125.98, 124.03, 123.73, 122.55, 121.42, 118.96, 114.14, 114.07, 113.69, 49.85, 20.21, 17.61. HRMS Calcd for C$_{31}$H$_{31}$N$_2$O: 447.2346. Found: 447.2346. [α]$_D^{25}$ −27.92° (c=1.018, MeOH).

The diamine hydrochloride salt (725 mg, 1.40 mmol) was suspended in 14 mL of triethylorthoformate (0.1 M) in a 25 mL round bottom flask. The vessel was equipped with a short-path distillation head and submerged into an oil bath preheated to 125° C. As the reaction proceeded, a sticky, gummy solid was deposited on the walls of the flask, in addition to clumps that form in the reaction mixture. The reaction mixture was stirred at 125° C. and the distillation head was heated periodically (approximately every 30 min) to ensure removal of ethanol over (typically 4 h), following which a white precipitate is obtained. After cooling the flask to 22° C., the mixture was diluted with 30 mL of Et$_2$O and filtered. The precipitate was washed with additional Et$_2$O (2×10 mL) and dried under vacuum (12 h) in an Abderhalden pistol charged with P$_2$O$_5$ over refluxing isopropanol (573 mg white solid, 83%). IR (KBr): 3422 (br), 2950 (m), 2839 (m), 2677 (w), 2590 (w), 1618 (s), 1590 (m), 1503 (m), 1478 (w), 1434 (w), 1344 (m), 1302 (w), 1276 (m), 1256 (s), 1225 (w), 1213 (w), 978 (w), 825 (w), 755 (w), 515 (w), 494 (w). $^1$H NMR (400 MHz, (CD$_3$)$_2$SO): δ 10.56 (br, 1H, ArOH), 8.67 (s, 1H, NCHN), 8.28 (d, J=8.6 Hz, 1H, aromatic H), 8.14 (d, J=8.2 Hz, 1H, aromatic H), 8.04 (d, J=9.0 Hz, 1H, aromatic H), 7.98 (d, J=8.8 Hz, 1H, aromatic H), 7.95 (d, J=8.2 Hz, 1H, aromatic H), 7.64–7.57 (m, 2H, aromatic H), 7.41 (ddd, J=8.4, 7.1, 1.1 Hz, 1H, aromatic H), 7.32 (ddd, J=8.0, 6.9, 1.1 Hz, 1H, aromatic H), 7.26 (ddd, J=8.2, 6.8, 1.3 Hz, 1H, aromatic H), 7.14 (d, J=8.4 Hz, 1H, aromatic H), 6.93 (br, 2H, mesityl aromatic H), 6.87 (d, J=8.2 Hz, 1H, aromatic H), 4.34 (dd, J=21.6, 10.4 Hz, 1H, ArNH$_2$CH$_2$), 4.20 (dd, J=21.6, 10.4 Hz, 1H, ArNH$_2$CH$_2$), 4.01 (dd, J=11.2, 10.4 Hz, 2H, ArNH$_2$CH$_2$), 2.20 (s, 3H, p-CH$_3$), 1.98 (br, 3H, o-CH$_3$), 1.71 (br, 3H, o-CH$_3$). $^{13}$C NMR (100 MHz, (CD$_3$)$_2$SO): δ 158.24, 153.40, 139.54, 135.25, 133.34, 133.23, 132.93, 132.40, 130.84, 130.75, 130.48, 129.73, 129.16, 128.39, 128.36, 127.97, 127.47, 127.31, 127.26, 126.21, 123.62, 123.37, 123.12, 118.51, 113.01, 51.28, 50.62, 20.46, 16.67. HRMS Calcd for C$_{32}$H$_{29}$N$_2$O (M−Cl): 457.2280. Found (FAB on C$_{32}$H$_{29}$ClN$_2$O): 457.2281. Anal. Calcd for C$_{32}$H$_{29}$ClN$_2$O: C, 77.95; H, 5.93; N, 5.68. Found: C, 77.68; H, 5.82; N, 5.59. [α]$_D^{25}$ −15.82° (c=0.9818, DMSO).

Example 13

Ruthenium complex (9). Cl$_2$Ru(=CH-o-OiPrC$_6$H$_4$)PPh$_3$ (14) (288 mg, 0.495 mmol), silver (I) carbonate (136 mg, 0.495 mmol), and the ligand salt (7) (244 mg, 0.495 mmol) were added to a 10 mL round bottom flask in a glove box. The vessel was removed from the box and the solids were suspended in 2.5 mL of THF and 2.5 mL of benzene (0.10 M). The flask was equipped with a reflux condenser and submerged into an oil bath preheated to 75° C. The reaction was stirred for 30 min, during which time the mixture remained heterogeneous but turned color from light pink to dark green/brown. The reaction mixture was then cooled to 22° C. and concentrated by a gentle N$_2$ purge. $^1$H NMR analysis of the crude reaction mixture revealed 91% conversion to a new singlet at 15.98 ppm corresponding to the carbene proton of 9. The metal carbene complex is isolated by column chromatogaphy (3 cm in diameter, 10 cm in length) on silica gel using CH$_2$Cl$_2$ as the eluant (R$_f$=0.10). Solvent removal under reduced pressure gave a brown solid residue (191 mg, 52%). Alternatively, concentrated CH$_2$Cl$_2$ solutions were triturated with hexanes or pentane to precipitate the catalyst as a light brown powder. IR (NaCl): 3049 (w), 2974 (w), 2917 (w), 1615 (w), 1588 (m), 1575 (w), 1559 (w), 1506 (w), 1490 (w), 1475 (s), 1455 (m), 1424 (s), 1404 (w), 1384 (w), 1374 (w), 1355 (m), 1342 (m), 1312 (w), 1296 (m), 1275 (s), 1239 (m), 1211 (w), 1155 (w), 1112 (m), 1097 (w), 981 (w), 937 (w), 839 (w), 825 (w), 784 (w), 746 (s), 684 (w). $^1$H NMR (400 MHz, CDCl$_3$): δ 15.96 (s, 1H, RuCH), 8.22 (d, J=8.7 Hz, 1H, aromatic H), 8.07 (d, J=8.6 Hz, 1H, aromatic H), 8.01 (d, J=8.4 Hz, 1H, aromatic H), 7.74 (d, J=7.6 Hz, 1H, aromatic H), 7.58 (d, J=9.0 Hz, 1H, aromatic H), 7.52 (ddd, J=8.1, 6.0, 2.1 Hz, 1H, aromatic H), 7.36 (ddd, J=8.2, 4.5, 4.1 Hz, 1H, aromatic H), 7.31–7.10 (m, 4H, aromatic H), 7.06 (br, 1H, aromatic H), 6.98 (br, 1H, aromatic H), 6.90 (s, 2H, mesityl aromatic H), 6.89 (s, 1H, aromatic H), 6.67 (d, J=8.6 Hz, 1H, aromatic H), 6.66 (d, J=8.9 Hz, 1H, aromatic H), 4.77 (septet, J=6.1 Hz, 1H, ArOCH(CH$_3$)$_2$), 4.28–4.22 (m, 1H, ArNH$_2$CH$_2$), 3.92–3.85 (m, 1H, ArNH$_2$CH$_2$), 3.61–3.48 (m, 2H, ArNH$_2$CH$_2$), 2.43 (s, 3H, o-CH$_3$), 2.22 (s, 3H, o-CH$_3$), 1.74 (s, 3H, p-CH$_3$), 1.05 (d, J=6.1 Hz, 3H, ArOCH(CH$_3$)$_2$), 0.56 (d, J=6.1 Hz, 3H, ArOCH(CH$_3$)$_2$). $^{13}$C NMR (100 MHz, CDCl$_3$): δ 281.62, 214.54, 169.96, 152.32, 144.30, 138.62, 138.36, 137.93, 137.40, 137.34, 137.12, 134.48, 134.41, 133.64, 129.79, 129.29, 128.89, 128.57, 128.49, 128.12, 127.98, 127.91, 127.84, 127.78, 126.81, 126.58, 125.88, 124.45, 122.44, 121.77, 121.63, 119.32, 112.98, 74.83, 52.88, 51.48, 21.27, 20.41, 20.39, 18.49, 18.00. HRMS Calcd for C$_{42}$H$_{39}$ClN$_2$O$_2$Ru: 740.1744. Found: 740.1746. Anal. Calcd for C$_{42}$H$_{39}$ClN$_2$O$_2$Ru: C, 68.14; H, 5.31; N, 3.78. Found: C, 67.89; H, 5.58; N, 3.55. [α]$_D^{25}$ −980.2° (c=0.1752, CHCl$_3$).

Example 14

Representative Procedure for Ring-Closing Metathesis with Catalyst (9). A 5 mL round bottom flask was charged with N-allyl-N-tosyl methacrylamide (15) (26.7 mg, 0.0956 mmol) and 6.8 mg (0.0092 mmol, 9.6 mol %) of racemic 9 in a glove box. The flask was removed from the box and the solids were dissolved in 0.96 mL of toluene (0.1 M). The vessel was equipped with a reflux condenser, submerged into an oil bath, and heated at 80° C. for 48 h. At this time, all starting material was consumed as indicated by TLC analysis. The dark brown solution was concentrated with a gentle N$_2$ purge, affording a dark brown crystalline solid. Column chromatography (3 cm in diameter and 10 cm high) in straight CH$_2$Cl$_2$ delivered the desired product (23.2 mg, 97%) and the recovered catalyst (6.2 mg, 91%) as white and brown solids, respectively. The catalyst residue was transferred directly into a clean 5 mL round bottom flask for subsequent reaction. A stream of N$_2$ was again used to concentrate this solution to a brown solid. The flask was loaded with fresh substrate (27.9 mg, 0.100 mmol) and the reaction was repeated as described above. $^1$H NMR analysis of the reaction mixture after 48 h at 80° C. revealed 93% conversion to product (16). Purification as described above again provided the product (22.6 mg, 90%) and recovered catalyst (5.8 mg, 78%) in high yields.

Example 15

Representative Procedure for AROM/CM of cis-5-Norbornene-endo-2,3-Dicarboxylic Anhydride. cis-5-Norbornene-endo-2,3-dicarboxylic anhydride (19) (12.2 mg, 0.0743 mmol), styrene (43 μl, 0.375 mmol, 5.0 equiv), and 9 (5.5 mg, 0.0074 mmol, 10 mol %) were combined in a 5 mL flask in a glove box. The flask was removed from the box and the solids were dissolved in 0.40 mL of THF (0.2 M). A reflux condenser was attached to the top of the vessel and the brown-colored solution was stirred for 1.5 h at 50° C. in an oil bath. At this time, no starting material was detectable by TLC analysis. Dry silica gel (750 mg) was then added to the reaction mixture, absorbing the full volume of solvent in the flask. Residual solvent was removed from the slurry under reduced pressure. The product-laden silica gel was loaded directly onto a column 3 cm in diameter and 15 cm high, and elution with 5:1 hexanes:EtOAc provided the product (20a) as a colorless oil (R$_f$=0.16, 14.2 mg, 71%) and the catalyst as a brown solid (R$_f$=0.20, 5.3 mg, 96%).

4-Styrenyl-6-vinyl-tetrahydro-cyclopenta[c]furan-1,3-dione (20a). IR (NaCl): 3081 (w), 3024 (w), 2960 (w), 2923 (m), 2853 (w), 1854 (s), 1776 (s), 1640 (w), 1602 (w), 1494 (w), 1449 (w), 1324 (w), 1257 (m), 1205 (s), 1089 (m), 1004 (s), 968 (s), 921 (s), 794 (m), 752 (m), 695 (m). $^1$H NMR (400 MHz, CDCl$_3$): δ 7.39 (d, J=7.0 Hz, 2H), 7.32 (t, J=7.3 Hz, 2H), 7.24 (t, J=7.3 Hz, 1H), 6.53 (d, J=15.8 Hz, 1H), 6.30 (dd, J=15.8, 7.9 Hz, 1H), 6.03–5.93 (m, 1H), 5.24 (d, J=1.0 Hz, 1H), 5.21 (dt, J=6.8, 1.0 Hz, 1H), 3.59–5.51 (m, 2H), 3.22–3.12 (m, 1H), 3.11–3.01 (m, 1H), 2.14 (dt, J=12.8, 5.4 Hz, 1H), 1.57 (quartet, J=12.8 Hz, 1H). $^{13}$C NMR (100 MHz, CDCl$_3$): δ 170.71, 170.69, 136.78, 134.92, 132.44, 128.75, 127.90, 126.62, 126.50, 117.57, 49.98, 49.56, 46.94, 46.37, 36.72. Anal. Calcd for C$_{17}$H$_{16}$O$_3$: C, 76.10; H, 6.01. Found: C, 76.16; H, 6.28.

4-Hept-1-enyl-6-vinyl-tetrahydro-cyclopenta[c]furan-1,3-dione (20b). IR (NaCl): 3055 (w), 2959 (s), 2927 (s), 2855 (s), 1855 (s), 1778 (s), 1642 (w), 1456 (m), 1378 (w), 1325 (m), 1264 (s), 1205 (s), 1092 (s), 1004 (s), 972 (s), 920 (s), 797 (s), 739 (s), 704 (s), 574 (m). $^1$H NMR (400 MHz, CDCl$_3$): δ 5.96 (ddd, J=16.7, 10.6, 7.3 Hz, 1H), 5.60 (dt, J=15.4, 6.4 Hz, 1H), 5.50 (dd, J=15.2, 7.5 Hz, 1H), 5.18 (s, 1H), 5.15 (dt, J=8.1, 1.1 Hz, 1H), 3.4 (quartet, J=8.4 Hz, 2H), 3.00–2.90 (m, 2H), 2.06–1.97 (m, 3H), 1.47–1.23 (m, 7H), 0.87 (t, J=6.9 Hz, 3H). $^{13}$C NMR (100 MHz, CDCl$_3$): δ 170.96, 170.71, 135.17, 133.92, 126.34, 117.26, 49.71, 49.67, 46.80, 46.11, 36.72, 32.50, 31.45, 28.98, 22.62, 14.17. HRMS Calcd for C$_{16}$H$_{22}$O$_3$: 262.1569. Found: 262.1569.

4-(2-Cyclohexyl-vinyl)-6-vinyl-tetrahydro-cyclopenta[c]furan-1,3-dione (20c). IR (NaCl): 2933 (s), 2848 (m), 1848 (m), 1785 (s), 1643 (w), 1445 (w), 1259 (w), 1199 (m), 1093 (s), 1004 (w), 969 (w), 960 (w), 929 (m), 792 (w). $^1$H NMR (400 MHz, CDCl$_3$): δ 5.96 (ddd, J=17.4, 10.8, 6.6 Hz, 1H), 5.55–5.41 (m, 2H), 5.18 (d, J=1.2 Hz, 1H), 5.15 (dt, J=7.9, 1.3 Hz, 1H), 3.44 (q, J=8.2 Hz, 2H), 3.00–2.89 (m, 2H), 2.04–1.91 (m, 2H), 1.76–1.58 (m, 4H), 1.42 (q, J=13.0 Hz, 1H), 1.32–0.98 (m, 6H). $^{13}$C NMR (100 MHz, CDCl$_3$): δ 170.97, 170.63, 139.58, 135.19, 124.02, 117.30, 49.80, 46.89, 46.10, 40.67, 36.69, 33.01, 32.98, 26.28, 26.13. HRMS Calcd for C$_{17}$H$_{22}$O$_3$: 274.1569. Found: 274.1571. Anal. Calcd for C$_{17}$H$_{22}$O$_3$: C, 74.42; H, 8.08. Found: C, 74.29; H, 7.95.

The 7-anti-norbornenyl aryl ethers reported herein were prepared under standard Mitsunobu etherification conditions from the appropriate phenol and 7-anti-norbornenol. These substitution reactions proceed with retention of configuration.

7-Anti-norbornenyl p-trifluorophenyl ether (21a). IR (NaCl): 3064 (w), 2979(m), 2945 (m), 2871 (w), 1617 (m), 1590 (w), 1518 (m), 1458 (w), 1423 (w), 1329 (s), 1311 (m), 1277 (w), 1256 (s), 1244 (s), 1161 (m), 1120 (s), 1109 (s), 1072 (w), 1048 (s), 1010 (w), 858 (w), 835 (m), 713 (m), 631 (m). $^1$H NMR (400 MHz, CDCl$_3$): δ 7.52 (d, J=9.1 Hz, 2H, aromatic H), 6.97 (d, J=9.1 Hz, 2H, aromatic H), 6.07 (t, J=2.2 Hz, 2H, olefinic H), 4.01 (s, 1H, ArOCH), 2.88–2.84 (m, 2H, ArOCH(CHR$^1$R$^2$)$_2$), 1.90–1.8 (m, 2H, aliphatic H), 1.07 (ddd, J=11.4, 3.8, 0.8 Hz, 2H, aliphatic H). $^{13}$C NMR (100 MHz, CDCl$_3$): δ 160.12, 133.97, 126.88 (q, J$_{CF}$=3.8 Hz), 115.27, 85.95, 43.69, 21.88. HRMS Calcd for C$_{14}$H$_{13}$F$_3$O: 254.0918. Found: 254.0918. Anal. Calcd for C$_{14}$H$_{13}$F$_3$O: C, 66.14; H, 5.15. Found: C, 66.36; H, 5.06.

7-Anti-norbornenyl p-methoxyphenyl ether (21b). IR (NaCl): 3060 (w), 2975 (m), 2944 (m), 2868 (w), 2833 (w), 1506 (s), 1464 (w), 1456 (w), 1442 (w), 1350 (w), 1335 (w), 1305 (w), 1258 (w), 1228 (s), 1181 (w), 1127 (w), 1106 (w), 1092 (w), 1065 (m), 1039 (m), 825 (m), 749 (m), 712 (m). $^1$H NMR (400 MHz, CDCl$_3$): δ 6.83 (ddt, J=18.3, 9.1, 2.8 Hz, 4H, aromatic H), 6.04 (t, J=2.2 Hz, 2H, olefinic H), 3.89 (br, 1H, ArOCH), 3.77 (s, 3H, ArOCH$_3$), 2.82–2.79 (m, 2H, ArOCH(CHR$^1$R$^2$)$_2$), 1.92–1.87 (m, 2H, aliphatic H), 1.04 (dd, J=10.5, 3.8 Hz, 2H, aliphatic H). $^{13}$C NMR (100 MHz, CDCl$_3$): δ 154.08, 151.77, 134.17, 116.77, 114.70, 86.97, 55.85, 43.82, 21.88. HRMS Calcd for C$_{14}$H$_{16}$O$_2$: 216.1150. Found: 216.1150. Anal. Calcd for C$_{14}$H$_{16}$O$_2$: C, 77.75; H, 7.46. Found: C, 77.48; H, 7.21.

Example 16

Representative Procedure for Room-Temperature AROM/CM of 7-Anti-Norbornenyl Aryl Ethers. 7-Anti-norbornenyl p-trifluoromethylphenyl ether (21a) (67.2 mg, 0.264 mmol) and styrene (55.8 mg, 0.536 mmol, 2.0 equiv) were weighed in air as neat oils into a 5 mL round bottom flask and dissolved in 2.6 mL of THF (0.1 M). Complex 9 (9.9 mg, 0.0134 mmol, 5 mol %) was then added directly to the colorless solution as a solid in one portion. The flask was stirred uncapped for 1 h at 22° C., at which point TLC analysis indicated that the reaction was complete. Dry silica gel (1.25 g) was added to the mixture in one portion. Residual solvent was removed from the resulting slurry at reduced pressure. The dry silica gel containing the product was then loaded directly onto a column (2.5 cm in diameter, 10 cm high) packed in CH$_2$Cl$_2$; elution with 100% CH$_2$Cl$_2$ provided the catalyst as a brown solid (R$_f$~0.10, 8.5 mg, 86%) and a crude mixture of non-polar organic products. This fraction was then rechromatographed over silica gel in 100:1 hexanes:Et$_2$O to give the desired product as a colorless oil (R$_f$=0.25, 62.4 mg, 66%).

2-Styrenyl-5-vinyl-cyclopentyl-p-trifluoromethylphenyl ether (22a). IR (NaCl): 2956 (w), 2929 (w), 2872 (w), 1615 (m), 1589 (w), 1517 (m), 1493 (w), 1449 (w), 1422 (w), 1327 (s), 1311 (m), 1253 (s), 1178 (m), 1161 (m), 1112 (s), 1068 (m), 1009 (m), 965 (w), 917 (w), 836 (m), 747 (m), 693 (m). $^1$H NMR (400 MHz, CDCl$_3$): δ 7.48 (d, J=8.4 Hz, 2H, aromatic H), 7.34–7.27 (m, 4H, aromatic H), 7.24–7.19 (m, 1H, aromatic H), 6.97 (d, J=8.4 Hz, 2H, aromatic H), 6.44 (dd, J=15.8, 1.0 Hz, 1H, PhCHCHR), 6.21 (dd, J=15.8, 8.0 Hz, 1H, PhCHCHR), 5.90 (ddd, J=18.2, 10.4, 7.8 Hz, 1H, RCHCH$_2$), 5.12 (ddd, J=17.2, 1.6, 1.4 Hz, 1H, RCHCH$_2$), 5.07 (ddd, J=10.2, 1.4, 1.0 Hz, 1H, RCHCH$_2$), 4.38 (t, J=5.1 Hz, 1H, ArOCH), 2.99–2.90 (m, 1H, ArOCH(CHR$^1$R$^2$)$_2$), 2.87–2.79 (m, 1H, ArOCH(CHR$^1$R$^2$)$_2$), 2.16–2.04 (m, 2H, aliphatic H), 1.79–1.67 (m, 2H, aliphatic H). $^{13}$C NMR (100 MHz, CDCl$_3$): δ 161.29, 139.69, 137.34, 131.41, 130.79, 128.72, 127.48, 126.90 (q, J$_{CF}$=3.9 Hz), 126.25, 116.29, 115.53, 89.23, 50.06, 49.71, 29.83, 29.41. HRMS Calcd for C$_{22}$H$_{21}$F$_3$O: 358.1544. Found: 358.1544. Anal. Calcd for C$_{22}$H$_{21}$F$_3$O: C, 73.73; H, 5.91. Found: C, 74.00; H, 6.20.

2-Styrenyl-5-vinyl-cyclopentyl-p-methoxyphenyl ether (22b). IR (NaCl): 2951 (m), 2931 (m), 2871 (w), 1506 (s), 1464 (w), 1448 (w), 1228 (s), 1180 (w), 1039 (m), 965 (w), 914 (w), 825 (m), 749 (m), 693 (m). $^1$H NMR (400 MHz, CDCl$_3$): δ 7.34–7.26 (m, 4H, aromatic H), 7.23–7.18 (m, 1H, aromatic H), 6.86 (d, J=9.2 Hz, 1H, aromatic H), 6.86 (dd, J=10.4, 6.1 Hz, 1H, aromatic H), 6.77 (d, J=9.2 Hz, 1H, aromatic H), 6.77 (dd, J=10.4, 6.1 Hz, 1H, aromatic H), 6.43 (dd, J=15.8, 0.8 Hz, 1H, PhCHCHR), 6.21 (dd, J=15.8, 8.2 Hz, 1H, PhCHCHR), 5.89 (ddd, J=18.0, 10.4, 7.6 Hz, 1H, RCHCH$_2$), 5.11 (dt, J=17.2, 1.6 Hz, 1H, RCHCH$_2$), 5.04 (ddd, J=10.4, 1.8, 1.2 Hz, 1H, RCHCH$_2$), 4.20 (t, J=5.7 Hz, 1H, ArOCH), 3.74 (s, 3H, ArOCH$_3$), 2.97–2.88 (m, 1H, ArOCH(CHR$^1$R$^2$)$_2$), 2.85–2.77 (m, 1H, ArOCH(CHR$^1$R$^2$)$_2$), 2.12–2.00 (m, 2H, aliphatic H), 1.74–1.62 (m, 2H, aliphatic H). $^{13}$C NMR (100 MHz, CDCl$_3$): δ 154.19, 152.96, 140.30, 137.65, 132.22, 130.31, 128.64, 127.25, 126.24, 118.19, 115.03, 114.61, 90.52, 55.82, 50.05, 49.67, 29.54, 29.09. HRMS Calcd for C$_{22}$H$_{24}$O$_2$: 320.1776. Found: 320.1776. Anal. Calcd for C$_{22}$H$_{24}$O$_2$: C, 82.46; H, 7.55. Found: C, 82.34; H, 7.80.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A chiral metal catalyst of formula (1):

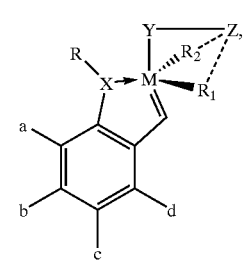

wherein:

M is a polyvalent metal;

X is oxygen (O) or sulfur (S);

R is selected from the group consisting of alkyl, alkenyl, alkynyl, aryl, aralkyl, alkoxy, alkenyloxy, alkynyloxy, aryloxy, alkoxy carbonyl, alkylamino, alkylthio, alkylsulfonyl, and alkylsulfinyl; wherein each is optionally substituted with an alkyl, halogen, alkoxy, aryl or heteroaryl group;

R$_1$ and R$_2$ are each independently an electron-withdrawing monovalent or divalent ligand provided at least one of them is a divalent ligand;

a, b, c, and d are each independently selected from the group consisting of hydrogen, halogen, alkyl, alkenyl, alkynyl, aryl, aralkyl, alkoxy, alkenyloxy, alkynyloxy, aryloxy, alkoxycarbonyl, alkylamino, alkylthio, alkylsulfunyl, and alkylsulfinyl; wherein each is independently optionally substituted with an alkyl, halogen, aryl or heteroaryl group;

Y is an electron-donating ligand; and

Z is an aromatic or heteroaromatic ring substituent that is bonded to Y and to either R$_1$ or R$_2$ provided either R$_1$ or R$_2$ is a divalent ligand.

2. The chiral metal catalyst of claim 1, wherein M is a transition metal.

3. The chiral metal catalyst of claim 2, wherein M is selected from the group consisting of ruthenium (Ru), rubidium (Rb), rhodium (Rh), molybdenum (Mo) or tungsten (W).

4. The chiral metal catalyst of claim 2, wherein M is ruthenium (Ru).

5. The chiral metal catalyst of claim 1, wherein R is a $C_1$–$C_{12}$ straight chain or branched alkyl group.

6. The chiral metal catalyst of claim 5, wherein R is isopropyl.

7. The chiral metal catalyst of claim 1, wherein $R_1$ or $R_2$ are each independently a dissimilar anionic electron-withdrawing monovalent or divalent ligand.

8. The chiral metal catalyst of claim 1, wherein $R_1$ or $R_2$ is a heteroatom.

9. The chiral metal catalyst of claim 8, wherein $R_1$ or $R_2$ is oxygen (O) or sulfur (S).

10. The chiral metal catalyst of claim 1, wherein $R_1$ or $R_2$ is a halogen.

11. The chiral metal catalyst of claim 10, wherein $R_1$ or $R_2$ is chlorine (Cl).

12. The chiral metal catalyst of claim 1, wherein a, b, c, and d are each independently hydrogen or a $C_1$–$C_{12}$ straight chain or branched alkyl group.

13. The chiral metal catalyst of claim 12, wherein a, b, c, and d are each hydrogen.

14. The chiral metal catalyst of claim 1, wherein X is oxygen (O).

15. The chiral metal catalyst of claim 1, wherein Y is a heteroaliphatic or heteroaromatic ligand, a carbene ligand, a phosphine ligand or a heterocyclic ring of formula (2):

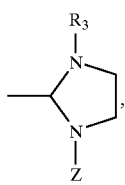

(2)

wherein:

$R_3$ is an aromatic ring; and

Z is an aromatic or heteroaromatic ring substituent.

16. The chiral metal catalyst of claim 15, wherein $R_3$ is a 2,4,6-trimethylphenyl group.

17. The chiral metal catalyst of claim 16, wherein Z is a 1,1'-binaphthalene group.

18. The chiral metal catalyst of claim 1, wherein Z is chiral.

19. The chiral metal catalyst of claim 1, wherein Z is a 1,1'-binaphthalene group.

20. A chiral metal catalyst of formula (3):

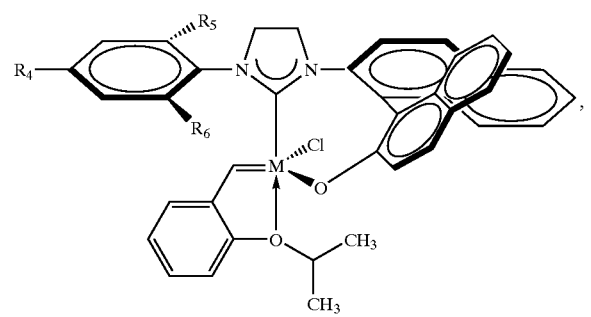

(3)

wherein:

M is a polyvalent metal; and $R_4$, $R_5$ and $R_6$ are each independently selected from the group consisting of hydrogen, alkyl, alkoxy, aryl or herteroaryl.

21. The chiral metal catalyst of claim 20, wherein M is a transition metal.

22. The chiral metal catalyst of claim 21, wherein M is selected from the group consisting of ruthenium (Ru), rubidium (Rb), rhodium (Rh), molybdenum (Mo) or tungsten (W).

23. The chiral metal catalyst of claim 21, wherein M is ruthenium (Ru).

24. The chiral metal catalyst of claim 20, wherein $R_4$, $R_5$ and $R_6$ are each independently a $C_1$–$C_{12}$ straight chain or branched alkyl group.

25. The chiral metal catalyst of claim 24, wherein $R_4$, $R_5$ and $R_6$ are each methyl.

26. The chiral metal catalyst of claim 20, wherein M is ruthenium (Ru) and $R_4$, $R_5$ and $R_6$ are each methyl.

27. A process of preparing a chiral metal catalyst of formula (3):

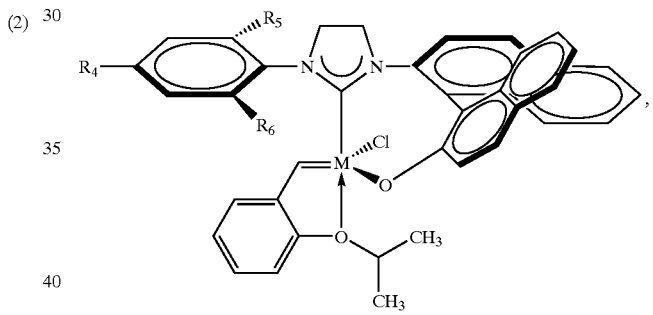

(3)

wherein:

M is a polyvalent metal; and $R_4$, $R_5$ and $R_6$ are each independently selected from the group consisting of hydrogen, alkyl, alkoxy, aryl or herteroaryl;

comprising the steps of:

a) reacting 1,1'-binapthyl-aminophenol (Formula (4)):

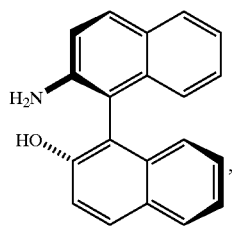

(4)

with aldehyde (5):

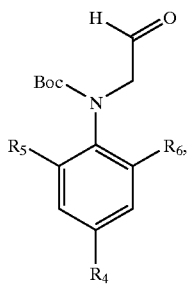
(5)

wherein $R_4$, $R_5$ and $R_6$ are as defined above, Boc is t-butoxycoarbonyl,
to form a compound of Formula (6):

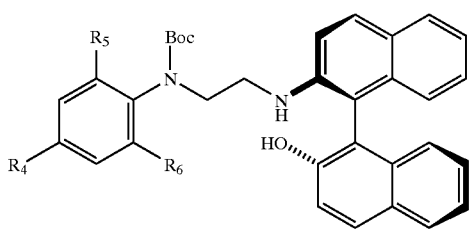
(6)

wherein $R_4$, $R_5$ and $R_6$ and Boc are as defined above;
b) reacting the compound of Formula (6) in the presence of an acid to form a compound of Formula (7):

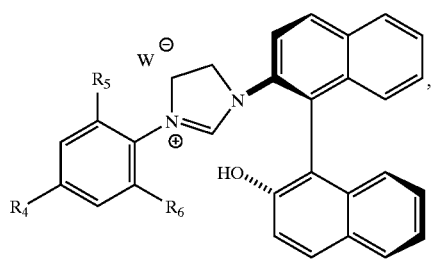
(7)

wherein W is a counter ion and $R_4$, $R_5$ and $R_6$ are as defined above;
c) reacting the compound of Formula (7) with a compound of Formula (8):

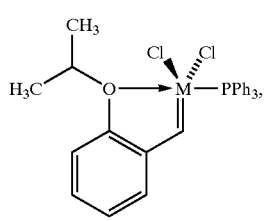
(8)

wherein M is as defined above,
to form the chiral transition metal catalyst of formula (3).

28. The process of claim 27, wherein M is a transition metal.

29. The process of claim 28, wherein M is selected from the group consisting of ruthenium (Ru), rubidium (Rb), rhodium (Rh), molybdenum (Mo) or tungsten (W).

30. The process of claim 28, wherein M is ruthenium (Ru).

31. The process of claim 27, wherein W is a halogen, phosphate or sulfate group.

32. The process of claim 31, wherein W is chlorine (Cl).

33. The process of claim 27, wherein $R_4$, $R_5$ and $R_6$ are each independently a $C_1$–$C_{12}$ straight chain or branched alkyl group.

34. The process of claim 33, wherein $R_4$, $R_5$ and $R_6$ are each methyl.

35. A method of obtaining a polysubstituted olefin via an enantioselective metathesis reaction using the chiral metal catalyst of claim 1.

36. The method of claim 35, wherein the enantioselective metathesis reaction is a ring-opening metathesis (ROM) reaction.

37. The method of claim 35, wherein the enantioselective metathesis reaction is a ring-closing metathesis (RCM) reaction.

38. The method of claim 35, wherein the enantioselective metathesis reaction is a asymmetric ring-opening/cross metathesis (AROM/CM) reaction.

39. A method of obtaining a polysubstituted olefin via an enantioselective metathesis reaction using the chiral metal catalyst of claim 1, wherein said chiral metal catalysts is recycled and reused multiple times.

40. The method of claim 39, wherein the enantioselective metathesis reaction is a ring-opening metathesis (ROM) reaction.

41. The method of claim 39, wherein the enantioselective metathesis reaction is a ring-closing metathesis (RCM) reaction.

42. The method of claim 39, wherein the enantioselective metathesis reaction is a asymmetric ring-opening/cross metathesis (AROM/CM) reaction.

43. The method of claim 39, wherein the chiral metal catalyst is recycled and reused multiple times in enantioselective metathesis reactions.

44. A method of obtaining a polysubstituted olefin via an enantioselective metathesis reaction using the chiral metal catalyst of claim 19.

45. The method of claim 44, wherein the enantioselective metathesis reaction is a ring-opening metathesis (ROM) reaction.

46. The method of claim 44, wherein the enantioselective metathesis reaction is a ring-closing metathesis (RCM) reaction.

47. The method of claim 44, wherein the enantioselective metathesis reaction is a ring-opening/cross metathesis (AROM/CM) reaction.

48. The method of claim 44, wherein the catalyst is recycled and reused multiple times in enantioselective metathesis reactions.

* * * * *